US011529396B2

(12) United States Patent
Bobadilla et al.

(10) Patent No.: US 11,529,396 B2
(45) Date of Patent: *Dec. 20, 2022

(54) TELOMERASE REVERSE TRANSCRIPTASE-BASED THERAPIES

(71) Applicants: FUNDACIÓN DEL SECTOR PÚBLICO ESTATAL CENTRO NACIONAL DE INVESTIGACIONES ONCOLÓGICAS CARLOS III (F.S.P. CNIO), Madrid (ES); UNIVERSITAT AUTÒNOMA DE BARCELONA, Bellaterra (ES)

(72) Inventors: Maria Bobadilla, Rosenau (FR); Ivan Formentini, Basel (CH); Maria Antonia Blasco Marhuenda, Madrid (ES); Christian Baer, Madrid (ES); Fàtima Bosch I Tubert, Bellaterra (ES)

(73) Assignees: FUNDACIÓN DEL SECTOR PÚBLICO ESTATAL CENTRO NACIONAL DL'INVESTIGACIONES ONCOLÓGICAS CARLOS III (F.S.P. CNIO), Madrid (ES); UNIVERSITAT AUTÒNOMA DE BARCELONA, Bellaterra (ES)

( * ) Notice: Subject to any disclaimer, the term of this patent is extended or adjusted under 35 U.S.C. 154(b) by 144 days.

This patent is subject to a terminal disclaimer.

(21) Appl. No.: 15/502,522

(22) PCT Filed: Aug. 4, 2015

(86) PCT No.: PCT/EP2015/067874
§ 371 (c)(1),
(2) Date: Feb. 8, 2017

(87) PCT Pub. No.: WO2016/020345
PCT Pub. Date: Feb. 11, 2016

(65) Prior Publication Data
US 2017/0232075 A1  Aug. 17, 2017

(30) Foreign Application Priority Data
Aug. 8, 2014  (EP) ..................... 14382312

(51) Int. Cl.
 A61K 48/00 (2006.01)
 A61K 38/45 (2006.01)
 A01K 67/027 (2006.01)
 C12N 9/12 (2006.01)

(52) U.S. Cl.
 CPC .......... *A61K 38/45* (2013.01); *A01K 67/0271* (2013.01); *A01K 67/0276* (2013.01); *A61K 48/005* (2013.01); *A61K 48/0058* (2013.01); *A61K 48/0066* (2013.01); *C12N 9/1276* (2013.01); *C12Y 207/07049* (2013.01); *A01K 2207/12* (2013.01); *A01K 2217/075* (2013.01); *A01K 2217/206* (2013.01); *A01K 2227/105* (2013.01); *A01K 2267/03* (2013.01); *A01K 2267/0381* (2013.01); *C12N 2750/14145* (2013.01)

(58) Field of Classification Search
None
See application file for complete search history.

(56) References Cited

U.S. PATENT DOCUMENTS

2005/0054093 A1* 3/2005 Haas ................ C12N 5/0605
435/366

FOREIGN PATENT DOCUMENTS

| EP | 2402038 A1 | 1/2012 | |
| WO | WO 09/061442 * | 5/2009 | ............. C12N 15/00 |
| WO | 2010/018731 A2 | 2/2010 | |

OTHER PUBLICATIONS

Bemelmans et al., PLOS One, 2013, 8: 1-9.*
Van Vliet et al., Methods in Molecular Biology, 2008, Chapter 2, p. 51-91.*
Chuhjo et al., Am. J. Hematol., 2008, 83: 387-389.*
Sequence alignment, 2019.*
Aksentijevich, Human Gene Therapy, 2008, 7: 1111-1122, Abstract.*
Beier, F. et al., Conditional TRF1 knockout in the hematopoietic compartment leads to bone marrow failure and recapitulates clinical features of Dyskeratosis congenita. Blood (2012).
Bernardes de Jesus, B. et al., Telomerase gene therapy in adult and old mice delays aging and increases longevity without increasing cancer. EMBO Mol Med 4 (2012): 1-14.
Blackburn, E. H., Switching and signaling at the telomere. Cell 106 (2001): 661-673.
Canela, A. et al., Telomere length analysis. Methods Mol Biol 371 (2007): 45-72.
Canela, A. et al., High-throughput telomere length quantification by FISH and its application to human population studies. Proc Natl Acad Sci U S A 104 (2007): 5300-5305.
De Lange, T., Shelterin: the protein complex that shapes and safeguards human telomeres. Genes Dev 19 (2005): 2100-2110.
Dokal, I., Dyskeratosis congenita. Hematology Am Soc Hematol Educ Program 2011 (2011): 480-486.
Dokal, I. et al., Inherited bone marrow failure syndromes. Haematologica 95 (2010): 1236-1240.

(Continued)

*Primary Examiner* — Ileana Popa
(74) *Attorney, Agent, or Firm* — Seed IP Law Group LLP

(57) ABSTRACT

The invention provides compositions and methods useful for the treatment and prevention of conditions associated with short telomere length.

7 Claims, 2 Drawing Sheets
Specification includes a Sequence Listing.

(56) References Cited

OTHER PUBLICATIONS

Flores, I. et al., The longest telomeres: a general signature of adult stem cell compartments. Genes Dev 22 (2008): 654-667.
Flores, I. et al., Effects of telomerase and telomere length on epidermal stem cell behavior. Science 309 (2005): 1253-1256.
Harley, C. B. et al., Telomeres shorten during ageing of human fibroblasts. Nature 345 (1990): 458-460.
Hiyama, E. et al., Telomere and telomerase in stem cells. Br J Cancer 96 (2007): 1020-1024.
Maciejewski, J. P. et al., Phenotypic and functional analysis of bone marrow progenitor cell compartment in bone marrow failure. Br J Haematol 87 (1994): 227-234.
Marsh, J. C. et al. Guidelines for the diagnosis and management of aplastic anaemia. Br J Haematol 147 (2009): 43-70.
Martinez, P. et al., Increased telomere fragility and fusions resulting from TRF1 deficiency lead to degenerative pathologies and increased cancer in mice. Genes Dev 23 (2009): 2060-2075.
Matsushita, T. et al., Adeno-associated virus vectors can be efficiently produced without helper virus. Gene Ther 5 (1998): 938-945.
Nakao, S., Immune mechanism of aplastic anemia. Int J Hematol 66 (1997): 127-134.
Samper, E. et al., Long-term repopulating ability of telomerase-deficient murine hematopoietic stem cells. Blood 99 (2002): 2767-2775.
Samper, E. et al., Mammalian Ku86 protein prevents telomeric fusions independently of the length of TTAGGG repeats and the G-strand overhang. EMBO Rep 1 (2000): 244-252.
Scopes, J. et al., Haemopoietic progenitor cells are reduced in aplastic anaemia. Br J Haematol 86 (1994): 427-430.
Vulliamy et al. Association between aplastic anaemia and mutations in telomerase RNA. Lancet 359 (2002): 2168-2170.
Wynn et al., Accelerated telomere shortening in young recipients of allogeneic bone-marrow transplants. Lancet 351 (1998): 178-181.
Young et al. (2006) Current concepts in the pathophysiology and treatment of aplastic anemia, BLOOD (2006)108, No. 8: 2509-2519.
Yamaguchi, M.D. et al. Mutations in TERT, the Gene for Telomerase Reverse Transcriptase, in Aplastic Anemia, the New England Journal of Mediine, 352, No. 14 (2005): 1413-1424.
International Search Report and Written Opinion for PCT/EP2015/067874, dated Oct. 1, 2015.
Armanios, M., An emerging role for the conserved telomere component 1 (CTC1) in human genetic disease. Pediatr Blood Cancer 59 (2012): 209-210.
Armanios, M. et al., The telomere syndromes. Nature reviews. Genetics 13 (2012): 693-704.
Ayuso, E. et al., High AAV vector purity results in serotype- and tissue-independent enhancement of transduction efficiency. Gene therapy 17 (2010): 503-510.
Bernardes de Jesus, B. et al., Telomerase gene therapy in adult and old mice delays aging and increases longevity without increasing cancer. EMBO molecular medicine 4 (2012): 691-704.
Bernardes de Jesus de Jesus et al., Telomerase at the intersection of cancer and aging. Trends Genet. 29 (2013): 513-520.
Blasco, M.A., Telomere length, stem cells and aging. Nature chemical biology 3 (2007): 640-649.
Blasco, M.A. et al., Telomere shortening and tumor formation by mouse cells lacking telomerase RNA. Cell 91 (1997): 25-34.
Buning, H. et al., Recent developments in adeno-associated virus vector technology. The journal of gene medicine 10 (2008): 717-733.
Calado, R.T. et al., Sex hormones, acting on the TERT gene, increase telomerase activity in human primary hematopoietic cells. Blood 114 (2009): 2236-2243.
Callen, E. et al., Breaks at telomeres and TRF2-independent end fusions in Fanconi anemia. Hum Mol Genet 11 (2002): 439-444.
Carroll, K.A. et al.,Telomere dysfunction in human diseases: the long and short of it! International journal of clinical and experimental pathology 2 (2009): 528-543.
Dokal, I., Dyskeratosis congenita. Hematology / the Education Program of the American Society of Hematology. American Society of Hematology. Education Program 2011 (2011): 480-486.
Duque, S. et al., Intravenous administration of self-complementary AAV9 enables transgene delivery to adult motor neurons. Molecular therapy : the journal of the American Society of Gene Therapy 17 (2009): 1187-1196.
Foust, K.D. etal., Intravascular AAV9 preferentially targets neonatal neurons and adult astrocytes. Nat Biotechnol 27 (2009): 59-65.
Gadalla, S.M. et al., Telomere length in blood, buccal cells, and fibroblasts from patients with inherited bone marrow failure syndromes. Aging (Albany NY) 2 (2010): 867-874.
Gao, G.P. et al., Novel adeno-associated viruses from rhesus monkeys as vectors for human gene therapy. Proc Natl Acad Sci U S A 99 (2002): 11854-11859.
Gonzalez-Suarez, E. et al., Increased epidermal tumors and increased skin wound healing in transgenic mice overexpressing the catalytic subunit of telomerase, mTERT, in basal keratinocytes. EMBO J 20 (2001): 2619-2630.
Herrera, E. et al., Disease states associated with telomerase deficiency appear earlier in mice with short telomeres. EMBO J 18 (1999): 2950-2960.
Holme, H. et al., Marked genetic heterogeneity in familial myelodysplasia/acute myeloid leukaemia. British journal of haematology 158 (2012): 242-248.
Inagaki, K. et al., Robust systemic transduction with AAV9 vectors in mice: efficient global cardiac gene transfer superior to that of AAV8. Molecular therapy : the journal of the American Society of Gene Therapy 14 (2006): 45-53.
Jaime-Perez, J.C. et al., Danazol as first-line therapy for aplastic anemia. Annals of hematology 90 (2011): 523-527.
Jaskelioff, M. et al., Telomerase reactivation reverses tissue degeneration in aged telomerase-deficient mice. Nature 469 (2011): 102-106.
Jiang, H. et al., Multiyear therapeutic benefit of AAV serotypes 2, 6, and 8 delivering factor VIII to hemophilia A mice and dogs. Blood 108 (2006): 107-115.
Kaplitt, M.G., Gene therapy clinical trials in the human brain. Protocol development and review of current applications. Frontiers of neurology and neuroscience 25 (2009): 180-188.
Kee, Y. et al., Molecular pathogenesis and clinical management of Fanconi anemia. J Clin Invest 122 (2012): 3799-3806.
Lee, H.W. et al., Essential role of mouse telomerase in highly proliferative organs. Nature 392 (1998): 569-574.
Maguire, A.M. et al., Safety and efficacy of gene transfer for Leber's congenital amaurosis. The New England journal of medicine 358 (2008): 2240-2248.
Manno, C.S. et al., Successful transduction of liver in hemophilia by AAV-Factor IX and limitations imposed by the host immune response. Nature medicine 12 (2006): 342-347.
Martinez, P. et al., Telomeric and extra-telomeric roles for telomerase and the telomere-binding proteins. Nature reviews. Cancer 11 (2011): 161-176.
Mas, A. et al., Reversal of type 1 diabetes by engineering a glucose sensor in skeletal muscle. Diabetes 55 (2006): 1546-1553.
Mason, P.J. et al., The genetics of dyskeratosis congenita. Cancer genetics 204 (2011): 635-645.
Matsushita, T. et al., Adeno-associated virus vectors can be efficiently produced without helper virus. Gene therapy 5 (1998): 938-945.
Mavilio, F., Gene therapies need new development models. Nature 490 (2012): 7.
Niemeyer, G.P. et al., Long-term correction of inhibitor-prone hemophilia B dogs treated with liver-directed AAV2-mediated factor IX gene therapy. Blood 113 (2009): 797-806.
O'Reilly, M. et al., NIH oversight of human gene transfer research involving retroviral, lentiviral, and adeno-associated virus vectors and the role of the NIH recombinant DNA advisory committee. Methods in enzymology 507 (2012): 313-335.

(56) References Cited

OTHER PUBLICATIONS

Samper, E. et al., Restoration of telomerase activity rescues chromosomal instability and premature aging in Terc-/-mice with short telomeres. EMBO Rep 2 (2001): 800-807.
Savage, S.A. et al., The role of telomere biology in bone marrow failure and other disorders. Mechanisms of ageing and development 129 (2008), 35-47.
Savage, S.A. et al., Genetic variation in telomeric repeat binding factors 1 and 2 in aplastic anemia. Experimental hematology 34 (2006): 664 671.
Stroes, E.S. et al., Intramuscular administration of AAV1-lipoprotein lipase S447X lowers triglycerides in lipoprotein lipase-deficient patients. Arteriosclerosis, thrombosis, and vascular biology 28 (2008): 2303-2304.
Tafuro, S. et al., Inducible adeno-associated virus vectors promote functional angiogenesis in adult organisms via regulated vascular endothelial growth factor expression. Cardiovascular research 83 (2009): 663-671.
Tomas-Loba, A. et al., Telomerase reverse transcriptase delays aging in cancer-resistant mice. Cell 135 (2008): 609-622.
Walne, A.J. et al., TINF2 mutations result in very short telomeres: analysis of a large cohort of patients with dyskeratosis congenita and related bone marrow failure syndromes. Blood 112 (2008): 3594-3600.
Yamaguchi, H. et al., Mutations of the human telomerase RNA gene (TERC) in aplastic anemia and myelodysplasia syndrome. Blood 102 (2003): 916-918.
Yamaguchi, H. et al., Mutations in TERT, the gene for telomerase reverse transcriptase, in aplastic anemia. The New England journal of medicine 352 (2005): 1413-1424.
Ziegler, P. et al., Telomere elongation and clinical response to androgen treatment in a patient with aplastic anemia and a heterozygous hTERT gene mutation. Annals of hematology 91 (2012): 1115-1120.
Ayuso, E. et al., Manufacturing and Characterization of a Recombinant Adeno-Associated Virus Type 8 Reference Standard Material. Hum Gene Ther. (2014).
Ayuso, E. et al. High AAV vector purity results in serotype- and tissue-independent enhancement of transduction efficiency. Gene Ther 17 (2010): 503-510.
Ball, S. E. et al., Progressive telomere shortening in aplastic anemia. Blood 91 (1998): 3582-3592.

\* cited by examiner

```
                            SEQUENCE LISTING

<160> NUMBER OF SEQ ID NOS: 26

<210> SEQ ID NO 1
<211> LENGTH: 4018
<212> TYPE: DNA
<213> ORGANISM: Homo sapiens

<400> SEQUENCE: 1
caggcagcgc tgcgtcctgc tgcgcacgtg ggaagccctg gccccggcca ccccgcgat       60 gccgcgcgct ccccgctgcc gagccgtgcg ctccctgctg cgcagccact accgcgaggt     120
gctgccgctg gccacgttcg tgcggcgcct ggggccccag ggctggcggc tggtgcagcg     180
cggggacccg gcggctttcc gcgcgctggt ggcccagtgc ctggtgtgcg tgccctggga     240
cgcacggccg cccccgccg ccccctcctt ccgccaggtg tcctgcctga aggagctggt     300
ggcccgagtg ctgcagaggc tgtgcgagcg cggcgcgaag aacgtgctgg ccttcggctt     360
cgcgctgctg gacggggccc gcggggggccc ccccgaggcc ttcaccacca gcgtgcgcag     420
ctacctgccc aacacggtga ccgacgcact gcgggggagc gggcgtggg ggctgctgct     480 gcgccgcgtg ggcgacgacg tgctggttca cctgctggca cgctgcgcgc tctttgtgct     540
ggtggctccc agctgcgcct accaggtgtg cgggccgccg ctgtaccagc tcggcgctgc     600
cactcaggcc cggcccccgc cacacgctag tggaccccga aggcgtctgg gatgcgaacg     660
ggcctggaac catagcgtca gggaggccgg ggtcccccctg ggcctgccag ccccgggtgc     720
gaggaggcgc gggggcagtg ccagccgaag tctgccgttg cccaagaggc ccaggcgtgg     780 cgctgccct gagccggagc ggacgcccgt tgggcagggg tcctgggccc acccgggcag     840
gacgcgtgga ccgagtgacc gtggtttctg tgtggtgtca cctgccagac ccgccgaaga     900
agccacctct ttggagggtg cgctctctgg cacgcgccac tcccacccat ccgtgggccg     960
ccagcaccac gcgggccccc catccacatc gcggccacca cgtccctggg acacgccttg    1020 tccccggtg tacgccgaga ccaagcactt cctctactcc tcaggcgaca aggagcagct    1080
gcggccctcc ttcctactca gctctctgag gcccagcctg actggcgctc ggaggctcgt    1140
ggagaccatc tttctgggtt ccaggccctg gatgccaggg actcccccgca ggttgccccg    1200 cctgcccag cgctactggc aaatgcggcc cctgtttctg gagctgcttg ggaaccacgc    1260
```

```
gcagtgcccc tacggggtgc tcctcaagac gcactgcccg ctgcgagctg cggtcacccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtgaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaaggt ggatgtgacg ggcgcgtacg acaccatccc   2220
ccaggacagg ctcacggagg tcatcgccag catcatcaaa ccccagaaca cgtactgcgt   2280
gcgtcggtat gccgtggtcc agaaggccgc ccatgggcac gtccgcaagg ccttcaagag   2340
ccacgtctct accttgacag acctccagcc gtacatgcga cagttcgtgg ctcacctgca   2400
ggagaccagc ccgctgaggg atgccgtcgt catcgagcag agctcctccc tgaatgaggc   2460
cagcagtggc ctcttcgacg tcttcctacg cttcatgtgc caccacgccg tgcgcatcag   2520
gggcaagtcc tacgtccagt gccaggggat cccgcagggc tccatcctct ccacgctgct   2580
ctgcagcctg tgctacggcg acatggagaa caagctgttt gcggggattc ggcgggacgg   2640
gctgctcctg cgtttggtgg atgatttctt gttggtgaca cctcacctca cccacgcgaa   2700
aaccttcctc aggaccctgg tccgaggtgt ccctgagtat ggctgcgtgg tgaacttgcg   2760
gaagacagtg gtgaacttcc ctgtagaaga cgaggccctg ggtggcacgg cttttgttca   2820
gatgccggcc cacggcctat tccctggtg cggcctgctg ctggataccc ggaccctgga   2880
ggtgcagagc gactactcca gctatgcccg gacctccatc agagccagtc tcaccttcaa   2940
ccgcggcttc aaggctggga ggaacatgcg tcgcaaactc tttggggtct gcggctgaa   3000 gtgtcacagc ctgtttctgg atttgcaggt gaacagcctc cagacggtgt gcaccaacat   3060
ctacaagatc ctcctgctgc aggcgtacag gtttcacgca tgtgtgctgc agctcccatt   3120
tcatcagcaa gtttggaaga accccacatt tttcctgcgc gtcatctctg acacggcctc   3180
cctctgctac tccatcctga aagccaagaa cgcagggatg tcgctggggg ccaagggcgc   3240
cgccggccct ctgccctccg aggccgtgca gtggctgtgc caccaagcat tcctgctcaa   3300
gctgactcga caccgtgtca cctacgtgcc actcctgggg tcactcagga cagcccagac   3360
gcagctgagt cggaagctcc cggggacgac gctgactgcc ctggaggccg cagccaaccc   3420
ggcactgccc tcagacttca agaccatcct ggactgatgg ccacccgccc acagccaggc   3480
cgagagcaga caccagcagc cctgtcacgc cgggctctac gtcccaggga gggaggggcg   3540
gcccacaccc aggcccgcac cgctgggagt ctgaggcctg agtgagtgtt tggccgaggc   3600
ctgcatgtcc ggctgaaggc tgagtgtccg gctgaggcct gagcgagtgt ccagccaagg   3660
```

-continued

```
gctgagtgtc cagcacacct gccgtcttca cttccccaca ggctggcgct cggctccacc    3720
ccagggccag cttttcctca ccaggagccc ggcttccact ccccacatag gaatagtcca    3780
tccccagatt cgccattgtt cacccctcgc cctgccctcc tttgccttcc accccaccca    3840
tccaggtgga gaccctgaga aggaccctgg gagctctggg aatttggagt gaccaaaggt    3900
gtgccctgta cacaggcgag gaccctgcac ctggatgggg gtccctgtgg gtcaaattgg    3960
ggggaggtgc tgtgggagta aaatactgaa tatatgagtt tttcagtttt gaaaaaaa     4018
```

```
<210> SEQ ID NO 2
<211> LENGTH: 1132
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Pro | Arg | Ala | Pro | Arg | Cys | Arg | Ala | Val | Arg | Ser | Leu | Leu | Arg | Ser |
| 1 | | | | 5 | | | | | 10 | | | | | 15 | |
| His | Tyr | Arg | Glu | Val | Leu | Pro | Leu | Ala | Thr | Phe | Val | Arg | Arg | Leu | Gly |
| | | | 20 | | | | | 25 | | | | | 30 | | |
| Pro | Gln | Gly | Trp | Arg | Leu | Val | Gln | Arg | Gly | Asp | Pro | Ala | Ala | Phe | Arg |
| | | | | 35 | | | | | 40 | | | | | 45 | |
| Ala | Leu | Val | Ala | Gln | Cys | Leu | Val | Cys | Val | Pro | Trp | Asp | Ala | Arg | Pro |
| | 50 | | | | | 55 | | | | | 60 | | | | |
| Pro | Pro | Ala | Ala | Pro | Ser | Phe | Arg | Gln | Val | Ser | Cys | Leu | Lys | Glu | Leu |
| 65 | | | | | 70 | | | | | 75 | | | | | 80 |
| Val | Ala | Arg | Val | Leu | Gln | Arg | Leu | Cys | Glu | Arg | Gly | Ala | Lys | Asn | Val |
| | | | | 85 | | | | | 90 | | | | | 95 | |
| Leu | Ala | Phe | Gly | Phe | Ala | Leu | Leu | Asp | Gly | Ala | Arg | Gly | Gly | Pro | Pro |
| | | | 100 | | | | | 105 | | | | | 110 | | |
| Glu | Ala | Phe | Thr | Thr | Ser | Val | Arg | Ser | Tyr | Leu | Pro | Asn | Thr | Val | Thr |
| | | | | 115 | | | | | 120 | | | | | 125 | |
| Asp | Ala | Leu | Arg | Gly | Ser | Gly | Ala | Trp | Gly | Leu | Leu | Leu | Arg | Arg | Val |
| | 130 | | | | | 135 | | | | | 140 | | | | |
| Gly | Asp | Asp | Val | Leu | Val | His | Leu | Leu | Ala | Arg | Cys | Ala | Leu | Phe | Val |
| 145 | | | | | 150 | | | | | 155 | | | | | 160 |
| Leu | Val | Ala | Pro | Ser | Cys | Ala | Tyr | Gln | Val | Cys | Gly | Pro | Pro | Leu | Tyr |
| | | | | 165 | | | | | 170 | | | | | 175 | |
| Gln | Leu | Gly | Ala | Ala | Thr | Gln | Ala | Arg | Pro | Pro | Pro | His | Ala | Ser | Gly |
| | | | 180 | | | | | 185 | | | | | 190 | | |
| Pro | Arg | Arg | Arg | Leu | Gly | Cys | Glu | Arg | Ala | Trp | Asn | His | Ser | Val | Arg |
| | | | | 195 | | | | | 200 | | | | | 205 | |
| Glu | Ala | Gly | Val | Pro | Leu | Gly | Leu | Pro | Ala | Pro | Gly | Ala | Arg | Arg | Arg |
| | 210 | | | | | 215 | | | | | 220 | | | | |
| Gly | Gly | Ser | Ala | Ser | Arg | Ser | Leu | Pro | Leu | Pro | Lys | Arg | Pro | Arg | Arg |
| 225 | | | | | 230 | | | | | 235 | | | | | 240 |
| Gly | Ala | Ala | Pro | Glu | Pro | Glu | Arg | Thr | Pro | Val | Gly | Gln | Gly | Ser | Trp |
| | | | | 245 | | | | | 250 | | | | | 255 | |
| Ala | His | Pro | Gly | Arg | Thr | Arg | Gly | Pro | Ser | Asp | Arg | Gly | Phe | Cys | Val |
| | | | 260 | | | | | 265 | | | | | 270 | | |
| Val | Ser | Pro | Ala | Arg | Pro | Ala | Glu | Glu | Ala | Thr | Ser | Leu | Glu | Gly | Ala |
| | | | | 275 | | | | | 280 | | | | | 285 | |
| Leu | Ser | Gly | Thr | Arg | His | Ser | His | Pro | Ser | Val | Gly | Arg | Gln | His | His |
| | 290 | | | | | 295 | | | | | 300 | | | | |
| Ala | Gly | Pro | Pro | Ser | Thr | Ser | Arg | Pro | Pro | Arg | Pro | Trp | Asp | Thr | Pro |

```
            305                 310                 315                 320
            Cys Pro Pro Val Ala Glu Thr Lys His Phe Leu Tyr Ser Ser Gly
                            325                 330                 335

Asp Lys Glu Gln Leu Arg Pro Ser Phe Leu Ser Ser Leu Arg Pro
                            340                 345                 350

Ser Leu Thr Gly Ala Arg Arg Leu Val Glu Thr Ile Phe Leu Gly Ser
                            355                 360                 365

Arg Pro Trp Met Pro Gly Thr Pro Arg Leu Pro Arg Leu Pro Gln
                370                 375                 380

Arg Tyr Trp Gln Met Arg Pro Leu Phe Leu Glu Leu Leu Gly Asn His
            385                 390                 395                 400

Ala Gln Cys Pro Tyr Gly Val Leu Leu Lys Thr His Cys Pro Leu Arg
                            405                 410                 415

Ala Ala Val Thr Pro Ala Ala Gly Val Cys Ala Arg Glu Lys Pro Gln
                            420                 425                 430

Gly Ser Val Ala Ala Pro Glu Glu Asp Thr Asp Pro Arg Arg Leu
                            435                 440                 445

Val Gln Leu Leu Arg Gln His Ser Ser Pro Trp Gln Val Tyr Gly Phe
                450                 455                 460

Val Arg Ala Cys Leu Arg Arg Leu Val Pro Pro Gly Leu Trp Gly Ser
            465                 470                 475                 480

Arg His Asn Glu Arg Arg Phe Leu Arg Asn Thr Lys Lys Phe Ile Ser
                            485                 490                 495

Leu Gly Lys His Ala Lys Leu Ser Leu Gln Glu Leu Thr Trp Lys Met
                            500                 505                 510

Ser Val Arg Asp Cys Ala Trp Leu Arg Arg Ser Pro Gly Val Gly Cys
                            515                 520                 525

Val Pro Ala Ala Glu His Arg Leu Arg Glu Glu Ile Leu Ala Lys Phe
                            530                 535                 540

Leu His Trp Leu Met Ser Val Tyr Val Val Glu Leu Leu Arg Ser Phe
            545                 550                 555                 560

Phe Tyr Val Thr Glu Thr Thr Phe Gln Lys Asn Arg Leu Phe Phe Tyr
                            565                 570                 575

Arg Lys Ser Val Trp Ser Lys Leu Gln Ser Ile Gly Ile Arg Gln His
                            580                 585                 590

Leu Lys Arg Val Gln Leu Arg Glu Leu Ser Glu Ala Glu Val Arg Gln
                            595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
            625                 630                 635                 640

Gly Ala Arg Thr Phe Arg Arg Glu Lys Arg Ala Glu Arg Leu Thr Ser
                            645                 650                 655

Arg Val Lys Ala Leu Phe Ser Val Leu Asn Tyr Glu Arg Ala Arg Arg
                            660                 665                 670

Pro Gly Leu Leu Gly Ala Ser Val Leu Gly Leu Asp Asp Ile His Arg
                            675                 680                 685

Ala Trp Arg Thr Phe Val Leu Arg Val Arg Ala Gln Asp Pro Pro
                690                 695                 700

Glu Leu Tyr Phe Val Lys Val Asp Val Thr Gly Ala Tyr Asp Thr Ile
            705                 710                 715                 720

Pro Gln Asp Arg Leu Thr Glu Val Ile Ala Ser Ile Ile Lys Pro Gln
                            725                 730                 735
```

```
Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Gly Pro Leu Pro Ser Glu Ala Val Gln Trp
            1060                1065                1070

Leu Cys His Gln Ala Phe Leu Leu Lys Leu Thr Arg His Arg Val Thr
        1075                1080                1085

Tyr Val Pro Leu Leu Gly Ser Leu Arg Thr Ala Gln Thr Gln Leu Ser
    1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130

<210> SEQ ID NO 3
<211> LENGTH: 3982
```

<212> TYPE: DNA
<213> ORGANISM: Homo sapiens

<400> SEQUENCE: 3

```
caggcagcgc tgcgtcctgc tgcgcacgtg ggaagccctg gccccggcca ccccgcgat      60
gccgcgcgct ccccgctgcc gagccgtgcg ctccctgctg cgcagccact accgcgaggt    120
gctgccgctg ccacgttcg tgcggcgcct ggggcccag ggctggcggc tggtgcagcg      180
cggggacccg gcggctttcc gcgcgctggt ggcccagtgc ctggtgtgcg tgccctggga    240
cgcacggccg ccccccgccg ccccctcctt ccgccaggtg tcctgcctga aggagctggt    300
ggcccgagtg ctgcagaggc tgtgcgagcg cggcgcgaag aacgtgctgg ccttcggctt    360
cgcgctgctg gacggggccc gcggggccc ccccgaggcc ttcaccacca gcgtgcgcag     420
ctacctgccc aacacggtga ccgacgcact gcggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggccccgc cacacgctag tggaccccga aggcgtctgg gatgcgaacg     660
ggcctggaac catagcgtca gggaggccgg ggtccccctg ggcctgccag ccccgggtgc    720
gaggaggcgc gggggcagtg ccagccgaag tctgccgttg cccaagaggc ccaggcgtgg    780
cgctgcccct gagccggagc ggacgcccgt tgggcagggg tcctgggccc acccgggcag   840
gacgcgtgga ccgagtgacc gtggtttctg tgtggtgtca cctgccagac cgccgaaga    900
agccacctct ttgagggtg cgctctctgg cacgcgccac tcccacccat ccgtgggccg     960
ccagcaccac gcgggccccc catccacatc gcggccacca cgtccctggg acacgccttg   1020
tccccggtg tacgccgaga ccaagcactt cctctactcc tcaggcgaca aggagcagct    1080
gcggccctcc ttcctactca gctctctgag gcccagcctg actggcgctc ggaggctcgt   1140
ggagaccatc tttctggggtt ccaggccctg gatgccaggg actccccgca ggttgccccg   1200
cctgccccag cgctactggc aaatgcggcc cctgtttctg gagctgcttg ggaaccacgc   1260
gcagtgcccc tacggggtgc tcctcaagac gcactgcccg ctgcgagctg cggtcaccccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact tgtcaagga caggctcacg gaggtcatcg ccagcatcat   2220
```

```
caaaccccag aacacgtact gcgtgcgtcg gtatgccgtg gtccagaagg ccgcccatgg    2280
gcacgtccgc aaggccttca agagccacgt ctctaccttg acagacctcc agccgtacat    2340
gcgacagttc gtggctcacc tgcaggagac cagcccgctg agggatgccg tcgtcatcga    2400
gcagagctcc tccctgaatg aggccagcag tggcctcttc gacgtcttcc tacgcttcat    2460
gtgccaccac gccgtgcgca tcaggggcaa gtcctacgtc cagtgccagg ggatcccgca    2520
gggctccatc ctctccacgc tgctctgcag cctgtgctac ggcgacatgg agaacaagct    2580 gttttgcgggg attcggcggg acgggctgct cctgcgtttg gtggatgatt tcttgttggt    2640
gacacctcac ctcacccacg cgaaaacctt cctcaggacc ctggtccgag gtgtccctga    2700
gtatggctgc gtggtgaact gcggaagac agtggtgaac ttccctgtag aagacgaggc    2760
cctgggtggc acggcttttg ttcagatgcc ggcccacggc ctattcccct ggtgcggcct    2820
gctgctggat acccggaccc tggaggtgca gagcgactac tccagctatg cccggacctc    2880
catcagagcc agtctcacct tcaaccgcgg cttcaaggct gggaggaaca tgcgtcgcaa    2940
actctttggg gtcttgcggc tgaagtgtca cagcctgttt ctggatttgc aggtgaacag    3000
cctccagacg gtgtgcacca acatctacaa gatcctcctg ctgcaggcgt acaggtttca    3060
cgcatgtgtg ctgcagctcc catttcatca gcaagtttgg aagaacccca cattttttcct    3120 gcgcgtcatc tctgacacgg cctccctctg ctactccatc ctgaaagcca gaacgcagg    3180 gatgtcgctg ggggccaagg gcgccgccgg ccctctgccc tccgaggccg tgcagtggct    3240
gtgccaccaa gcattcctgc tcaagctgac tcgacaccgt gtcacctacg tgccactcct    3300
ggggtcactc aggacagccc agacgcagct gagtcggaag ctcccgggga cgacgctgac    3360
tgccctggag gccgcagcca acccggcact gccctcagac ttcaagacca tcctggactg    3420
atggccaccc gcccacagcc aggccgagag cagacaccag cagccctgtc acgccgggct    3480
ctacgtccca gggagggagg ggcggcccac acccaggccc gcaccgctgg gagtctgagg    3540
cctgagtgag tgtttggccg aggcctgcat gtccggctga aggctgagtg tccggctgag    3600
gcctgagcga gtgtccagcc aagggctgag tgtccagcac acctgccgtc ttcacttccc    3660
cacaggctgg cgctcggctc caccccaggg ccagcttttc ctcaccagga gcccggcttc    3720
cactccccac ataggaatag tccatcccca gattcgccat tgttcacccc tcgccctgcc    3780
ctcctttgcc ttccacccc accatccagg tggagaccct gagaaggacc ctgggagctc    3840
tgggaatttg gagtgaccaa aggtgtgccc tgtacacagg cgaggaccct gcacctggat    3900
gggggtccct gtgggtcaaa ttgggggggag gtgctgtggg agtaaaatac tgaatatatg    3960 agttttttcag ttttgaaaaa aa                                            3982
```

<210> SEQ ID NO 4
<211> LENGTH: 1120
<212> TYPE: PRT
<213> ORGANISM: Homo sapiens

<400> SEQUENCE: 4

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60
```

```
Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
            245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
            325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
    355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
            405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480
```

```
Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Asp Arg Leu Thr Glu Val Ile Ala Ser Ile
705                 710                 715                 720

Ile Lys Pro Gln Asn Thr Tyr Cys Val Arg Arg Tyr Ala Val Val Gln
                725                 730                 735

Lys Ala Ala His Gly His Val Arg Lys Ala Phe Lys Ser His Val Ser
            740                 745                 750

Thr Leu Thr Asp Leu Gln Pro Tyr Met Arg Gln Phe Val Ala His Leu
        755                 760                 765

Gln Glu Thr Ser Pro Leu Arg Asp Ala Val Val Ile Glu Gln Ser Ser
    770                 775                 780

Ser Leu Asn Glu Ala Ser Ser Gly Leu Phe Asp Val Phe Leu Arg Phe
785                 790                 795                 800

Met Cys His His Ala Val Arg Ile Arg Gly Lys Ser Tyr Val Gln Cys
                805                 810                 815

Gln Gly Ile Pro Gln Gly Ser Ile Leu Ser Thr Leu Leu Cys Ser Leu
            820                 825                 830

Cys Tyr Gly Asp Met Glu Asn Lys Leu Phe Ala Gly Ile Arg Arg Asp
        835                 840                 845

Gly Leu Leu Leu Arg Leu Val Asp Asp Phe Leu Leu Val Thr Pro His
    850                 855                 860

Leu Thr His Ala Lys Thr Phe Leu Arg Thr Leu Val Arg Gly Val Pro
865                 870                 875                 880

Glu Tyr Gly Cys Val Val Asn Leu Arg Lys Thr Val Val Asn Phe Pro
                885                 890                 895

Val Glu Asp Glu Ala Leu Gly Gly Thr Ala Phe Val Gln Met Pro Ala
```

His Gly Leu Phe Pro Trp Cys Gly Leu Leu Asp Thr Arg Thr Leu
        915                 920                 925

Glu Val Gln Ser Asp Tyr Ser Tyr Ala Arg Thr Ser Ile Arg Ala
        930                 935                 940

Ser Leu Thr Phe Asn Arg Gly Phe Lys Ala Gly Arg Asn Met Arg Arg
945                 950                 955                 960

Lys Leu Phe Gly Val Leu Arg Leu Lys Cys His Ser Leu Phe Leu Asp
                965                 970                 975

Leu Gln Val Asn Ser Leu Gln Thr Val Cys Thr Asn Ile Tyr Lys Ile
                980                 985                 990

Leu Leu Leu Gln Ala Tyr Arg Phe His Ala Cys Val Leu Gln Leu Pro
        995                 1000                1005

Phe His Gln Gln Val Trp Lys Asn Pro Thr Phe Phe Leu Arg Val Ile
        1010                1015                1020

Ser Asp Thr Ala Ser Leu Cys Tyr Ser Ile Leu Lys Ala Lys Asn Ala
1025                1030                1035                1040

Gly Met Ser Leu Gly Ala Lys Gly Ala Ala Gly Pro Leu Pro Ser Glu
                1045                1050                1055

Ala Val Gln Trp Leu Cys His Gln Ala Phe Leu Leu Lys Leu Thr Arg
        1060                1065                1070

His Arg Val Thr Tyr Val Pro Leu Leu Gly Ser Leu Arg Thr Ala Gln
        1075                1080                1085

Thr Gln Leu Ser Arg Lys Leu Pro Gly Thr Thr Leu Thr Ala Leu Glu
        1090                1095                1100

Ala Ala Ala Asn Pro Ala Leu Pro Ser Asp Phe Lys Thr Ile Leu Asp
1105                1110                1115                1120

<210> SEQ ID NO 5
<211> LENGTH: 3426
<212> TYPE: DNA
<213> ORGANISM: Mus musculus

<400> SEQUENCE: 5

| | | |
|---|---|---|
| gtgggaggcc catcccggcc ttgagcacaa tgacccgcgc tcctcgttgc cccgcggtgc | 60 |
| gctctctgct gcgcagccga taccgggagg tgtggccgct ggcaaccttt gtgcggcgcc | 120 |
| tggggcccga gggcaggcgg cttgtgcaac ccggggaccc gaagatctac cgcactttgg | 180 |
| ttgcccaatg cctagtgtgc atgcactggg gctcacagcc tccacctgcc gacctttcct | 240 |
| tccaccaggt gtcatccctg aaagagctgg tggccagggt tgtgcagaga ctctgcgagc | 300 |
| gcaacgagag aaacgtgctg gcttttggct ttgagctgct taacgaggcc agaggcgggc | 360 |
| ctcccatggc cttcactagt agcgtgcgta gctacttgcc caacactgtt attgagaccc | 420 |
| tgcgtgtcag tggtgcatgg atgctactgt tgagccgagt gggcgacgac ctgctggtct | 480 |
| acctgctggc acactgtgct ctttatcttc tggtgccccc cagctgtgcc taccaggtgt | 540 |
| gtgggtctcc cctgtaccaa atttgtgcca ccacggatat ctggccctct gtgtccgcta | 600 |
| gttacaggcc cacccgaccc gtgggcagga atttcactaa ccttaggttc ttacaacaga | 660 |
| tcaagagcag tagtcgccag gaagcaccga aaccctggc cttgccatct cgaggtacaa | 720 |
| agaggcatct gagtctcacc agtacaagtg tgccttcagc taagaaggcc agatgctatc | 780 |
| ctgtcccgag agtggaggag ggaccccaca ggcaggtgct accaacccca tcaggcaaat | 840 |
| catgggtgcc aagtcctgct cggtcccccg aggtgcctac tgcagagaaa gatttgtctt | 900 |

```
ctaaaggaaa ggtgtctgac ctgagtctct ctgggtcggt gtgctgtaaa cacaagccca    960
gctccacatc tctgctgtca ccaccccgcc aaaatgcctt tcagctcagg ccatttattg   1020
agaccagaca tttcctttac tccaggggag atggccaaga gcgtctaaac ccctcattcc   1080
tactcagcaa cctccagcct aacttgactg gggccaggag actggtggag atcatctttc   1140
tgggctcaag gcctaggaca tcaggaccac tctgcaggac acaccgtcta tcgcgtcgat   1200
actggcagat gcggcccctg ttccaacagc tgctggtgaa ccatgcagag tgccaatatg   1260
tcagactcct caggtcacat tgcaggtttc gaacagcaaa ccaacaggtg acagatgcct   1320
tgaacaccag cccaccgcac ctcatggatt tgctccgcct gcacagcagt ccctggcagg   1380
tatatggttt tcttcgggcc tgtctctgca aggtggtgtc tgctagtctc tggggtacca   1440
ggcacaatga gcgccgcttc tttaagaact taaagaagtt catctcgttg gggaaatacg   1500
gcaagctatc actgcaggaa ctgatgtgga agatgaaagt agaggattgc cactggctcc   1560
gcagcagccc ggggaaggac cgtgtccccg ctgcagagca ccgtctgagg gagaggatcc   1620
tggctacgtt cctgttctgg ctgatggaca catacgtggt acagctgctt aggtcattct   1680
tttacatcac agagagcaca ttccagaaga acaggctctt cttctaccgt aagagtgtgt   1740
ggagcaagct gcagagcatt ggagtcaggc aacaccttga gagtgcggg ctacgggagc   1800
tgtcacaaga ggaggtcagg catcaccagg acacctggct agccatgccc atctgcagac   1860
tgcgcttcat ccccaagccc aacgcctgc ggcccattgt gaacatgagt tatagcatgg   1920
gtaccagagc tttgggcaga aggaagcagg cccagcattt cacccagcgt ctcaagactc   1980
tcttcagcat gctcaactat gagcggacaa acatcctca ccttatgggg tcttctgtac   2040
tgggtatgaa tgacatctac aggacctggc gggcctttgt gctgcgtgtg cgtgctctgg   2100
accagacacc caggatgtac tttgttaagg cagatgtgac cggggcctat gatgccatcc   2160
cccagggtaa gctggtggag gttgttgcca atatgatcag gcactcggag agcacgtact   2220
gtatccgcca gtatgcagtg gtccggagag atagccaagg ccaagtccac aagtccttta   2280
ggagacaggt caccacccctc tctgacctcc agccatacat gggccagttc cttaagcatc   2340
tgcaggattc agatgccagt gcactgagga actccgttgt catcgagcag agcatctcta   2400
tgaatgagag cagcagcagc ctgtttgact tcttcctgca cttcctgcgt cacagtgtcg   2460
taaagattgg tgacaggtgc tatacgcagt gccaggcat ccccaggc tccagcctat   2520
ccaccctgct ctgcagtctg tgtttcggag acatggagaa caagctgttt gctgaggtgc   2580
agcgggatgg gttgctttta cgttttgttg atgactttct gttggtgacg cctcacttgg   2640
accaagcaaa aaccttcctc agcaccctgg tccatggcgt tcctgagtat gggtgcatga   2700
taaacttgca gaagacagtg gtgaacttcc ctgtggagcc tggtaccctg ggtggtgcag   2760
ctccatacca gctgcctgct cactgcctgt ttccctggtg tggcttgctg ctggacactc   2820
agactttgga ggtgttctgt gactactcag gttatgccca gacctcaatt aagacgagcc   2880
tcaccttcca gagtgtcttc aaagctggga agaccatgcg gaacaagctc ctgtcggtct   2940
tgcggttgaa gtgtcacggt ctatttctag acttgcaggt gaacagcctc cagacagtct   3000
gcatcaatat atacaagatc ttcctgcttc aggcctacag gttccatgca tgtgtgattc   3060
agcttccctt tgaccagcgt gttaggaaga acctcacatt ctttctgggc atcatctcca   3120
gccaagcatc ctgctgctat gctatcctga aggtcaagaa tccaggaatg acactaaagg   3180
cctctggctc ctttcctcct gaagccgcac attggctctg ctaccaggcc ttcctgctca   3240
agctggctgc tcattctgtc atctacaaat gtctcctggg acctctgagg acagcccaaa   3300
```

```
aactgctgtg ccggaagctc ccagaggcga caatgaccat ccttaaagct gcagctgacc    3360
cagccctaag cacagacttt cagaccattt tggactaacc ctgtctcctt ccgctagatg    3420
aacatg                                                                3426
```

```
<210> SEQ ID NO 6
<211> LENGTH: 1122
<212> TYPE: PRT
<213> ORGANISM: Mus musculus

<400> SEQUENCE: 6
```

```
Met Thr Arg Ala Pro Arg Cys Pro Ala Val Arg Ser Leu Leu Arg Ser
1               5                   10                  15

Arg Tyr Arg Glu Val Trp Pro Leu Ala Thr Phe Val Arg Arg Leu Gly
            20                  25                  30

Pro Glu Gly Arg Arg Leu Val Gln Pro Gly Asp Pro Lys Ile Tyr Arg
        35                  40                  45

Thr Leu Val Ala Gln Cys Leu Val Cys Met His Trp Gly Ser Gln Pro
    50                  55                  60

Pro Pro Ala Asp Leu Ser Phe His Gln Val Ser Ser Leu Lys Glu Leu
65                  70                  75                  80

Val Ala Arg Val Val Gln Arg Leu Cys Glu Arg Asn Glu Arg Asn Val
                85                  90                  95

Leu Ala Phe Gly Phe Glu Leu Leu Asn Glu Ala Arg Gly Gly Pro Pro
            100                 105                 110

Met Ala Phe Thr Ser Ser Val Arg Ser Tyr Leu Pro Asn Thr Val Ile
        115                 120                 125

Glu Thr Leu Arg Val Ser Gly Ala Trp Met Leu Leu Leu Ser Arg Val
    130                 135                 140

Gly Asp Asp Leu Leu Val Tyr Leu Leu Ala His Cys Ala Leu Tyr Leu
145                 150                 155                 160

Leu Val Pro Pro Ser Cys Ala Tyr Gln Val Cys Gly Ser Pro Leu Tyr
                165                 170                 175

Gln Ile Cys Ala Thr Thr Asp Ile Trp Pro Ser Val Ser Ala Ser Tyr
            180                 185                 190

Arg Pro Thr Arg Pro Val Gly Arg Asn Phe Thr Asn Leu Arg Phe Leu
        195                 200                 205

Gln Gln Ile Lys Ser Ser Arg Gln Glu Ala Pro Lys Pro Leu Ala
    210                 215                 220

Leu Pro Ser Arg Gly Thr Lys Arg His Leu Ser Leu Thr Ser Thr Ser
225                 230                 235                 240

Val Pro Ser Ala Lys Lys Ala Arg Cys Tyr Pro Val Pro Arg Val Glu
                245                 250                 255

Glu Gly Pro His Arg Gln Val Leu Pro Thr Pro Ser Gly Lys Ser Trp
            260                 265                 270

Val Pro Ser Pro Ala Arg Ser Pro Glu Val Pro Thr Ala Glu Lys Asp
        275                 280                 285

Leu Ser Ser Lys Gly Lys Val Ser Asp Leu Ser Leu Ser Gly Ser Val
    290                 295                 300

Cys Cys Lys His Lys Pro Ser Ser Thr Ser Leu Leu Ser Pro Pro Arg
305                 310                 315                 320

Gln Asn Ala Phe Gln Leu Arg Pro Phe Ile Glu Thr Arg His Phe Leu
                325                 330                 335

Tyr Ser Arg Gly Asp Gly Gln Glu Arg Leu Asn Pro Ser Phe Leu Leu
```

```
                340             345             350
Ser Asn Leu Gln Pro Asn Leu Thr Gly Ala Arg Arg Leu Val Glu Ile
            355                 360                 365

Ile Phe Leu Gly Ser Arg Pro Arg Thr Ser Gly Pro Leu Cys Arg Thr
370                 375                 380

His Arg Leu Ser Arg Arg Tyr Trp Gln Met Arg Pro Leu Phe Gln Gln
385                 390                 395                 400

Leu Leu Val Asn His Ala Glu Cys Gln Tyr Val Arg Leu Leu Arg Ser
                405                 410                 415

His Cys Arg Phe Arg Thr Ala Asn Gln Gln Val Thr Asp Ala Leu Asn
            420                 425                 430

Thr Ser Pro Pro His Leu Met Asp Leu Leu Arg Leu His Ser Ser Pro
        435                 440                 445

Trp Gln Val Tyr Gly Phe Leu Arg Ala Cys Leu Cys Lys Val Val Ser
    450                 455                 460

Ala Ser Leu Trp Gly Thr Arg His Asn Glu Arg Arg Phe Phe Lys Asn
465                 470                 475                 480

Leu Lys Lys Phe Ile Ser Leu Gly Lys Tyr Gly Lys Leu Ser Leu Gln
                485                 490                 495

Glu Leu Met Trp Lys Met Lys Val Glu Asp Cys His Trp Leu Arg Ser
            500                 505                 510

Ser Pro Gly Lys Asp Arg Val Pro Ala Ala Glu His Arg Leu Arg Glu
        515                 520                 525

Arg Ile Leu Ala Thr Phe Leu Phe Trp Leu Met Asp Thr Tyr Val Val
    530                 535                 540

Gln Leu Leu Arg Ser Phe Phe Tyr Ile Thr Glu Ser Thr Phe Gln Lys
545                 550                 555                 560

Asn Arg Leu Phe Phe Tyr Arg Lys Ser Val Trp Ser Lys Leu Gln Ser
                565                 570                 575

Ile Gly Val Arg Gln His Leu Glu Arg Val Arg Leu Arg Glu Leu Ser
            580                 585                 590

Gln Glu Glu Val Arg His His Gln Asp Thr Trp Leu Ala Met Pro Ile
        595                 600                 605

Cys Arg Leu Arg Phe Ile Pro Lys Pro Asn Gly Leu Arg Pro Ile Val
    610                 615                 620

Asn Met Ser Tyr Ser Met Gly Thr Arg Ala Leu Gly Arg Arg Lys Gln
625                 630                 635                 640

Ala Gln His Phe Thr Gln Arg Leu Lys Thr Leu Phe Ser Met Leu Asn
                645                 650                 655

Tyr Glu Arg Thr Lys His Pro His Leu Met Gly Ser Ser Val Leu Gly
            660                 665                 670

Met Asn Asp Ile Tyr Arg Thr Trp Arg Ala Phe Val Leu Arg Val Arg
        675                 680                 685

Ala Leu Asp Gln Thr Pro Arg Met Tyr Phe Val Lys Ala Asp Val Thr
    690                 695                 700

Gly Ala Tyr Asp Ala Ile Pro Gln Gly Lys Leu Val Glu Val Val Ala
705                 710                 715                 720

Asn Met Ile Arg His Ser Glu Ser Thr Tyr Cys Ile Arg Gln Tyr Ala
                725                 730                 735

Val Val Arg Arg Asp Ser Gln Gly Gln Val His Lys Ser Phe Arg Arg
            740                 745                 750

Gln Val Thr Thr Leu Ser Asp Leu Gln Pro Tyr Met Gly Gln Phe Leu
        755                 760                 765
```

```
Lys His Leu Gln Asp Ser Asp Ala Ser Ala Leu Arg Asn Ser Val Val
770                 775                 780
Ile Glu Gln Ser Ile Ser Met Asn Glu Ser Ser Ser Leu Phe Asp
785                 790                 795                 800
Phe Phe Leu His Phe Leu Arg His Ser Val Val Lys Ile Gly Asp Arg
            805                 810                 815
Cys Tyr Thr Gln Cys Gln Gly Ile Pro Gln Gly Ser Ser Leu Ser Thr
            820                 825                 830
Leu Leu Cys Ser Leu Cys Phe Gly Asp Met Glu Asn Lys Leu Phe Ala
            835                 840                 845
Glu Val Gln Arg Asp Gly Leu Leu Arg Phe Val Asp Asp Phe Leu
850                 855                 860
Leu Val Thr Pro His Leu Asp Gln Ala Lys Thr Phe Leu Ser Thr Leu
865                 870                 875                 880
Val His Gly Val Pro Glu Tyr Gly Cys Met Ile Asn Leu Gln Lys Thr
            885                 890                 895
Val Val Asn Phe Pro Val Glu Pro Gly Thr Leu Gly Gly Ala Ala Pro
            900                 905                 910
Tyr Gln Leu Pro Ala His Cys Leu Phe Pro Trp Cys Gly Leu Leu Leu
            915                 920                 925
Asp Thr Gln Thr Leu Glu Val Phe Cys Asp Tyr Ser Gly Tyr Ala Gln
930                 935                 940
Thr Ser Ile Lys Thr Ser Leu Thr Phe Gln Ser Val Phe Lys Ala Gly
945                 950                 955                 960
Lys Thr Met Arg Asn Lys Leu Leu Ser Val Leu Arg Leu Lys Cys His
            965                 970                 975
Gly Leu Phe Leu Asp Leu Gln Val Asn Ser Leu Gln Thr Val Cys Ile
            980                 985                 990
Asn Ile Tyr Lys Ile Phe Leu Leu Gln Ala Tyr Arg Phe His Ala Cys
            995                 1000                1005
Val Ile Gln Leu Pro Phe Asp Gln Arg Val Arg Lys Asn Leu Thr Phe
            1010                1015                1020
Phe Leu Gly Ile Ile Ser Ser Gln Ala Ser Cys Cys Tyr Ala Ile Leu
1025                1030                1035                1040
Lys Val Lys Asn Pro Gly Met Thr Leu Lys Ala Ser Gly Ser Phe Pro
            1045                1050                1055
Pro Glu Ala Ala His Trp Leu Cys Tyr Gln Ala Phe Leu Leu Lys Leu
            1060                1065                1070
Ala Ala His Ser Val Ile Tyr Lys Cys Leu Leu Gly Pro Leu Arg Thr
            1075                1080                1085
Ala Gln Lys Leu Leu Cys Arg Lys Leu Pro Glu Ala Thr Met Thr Ile
            1090                1095                1100
Leu Lys Ala Ala Ala Asp Pro Ala Leu Ser Thr Asp Phe Gln Thr Ile
1105                1110                1115                1120
Leu Asp

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
```

|  |  |
|---|---|
| ggcaccacac cttctacaat g | 21 |

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8

|  |  |
|---|---|
| gtggtggtga agctgtag | 18 |

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9

|  |  |
|---|---|
| ggattgccac tggctccg | 18 |

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10

|  |  |
|---|---|
| tgcctgacct cctcttgtga c | 21 |

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11

|  |  |
|---|---|
| cgtaccccga ttcaggtgat | 20 |

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12

|  |  |
|---|---|
| ttgagcagaa gagctgctac gt | 22 |

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13

|  |  |
|---|---|
| ggcaaagtgg agaggatcga c | 21 |

<210> SEQ ID NO 14
<211> LENGTH: 18
<212> TYPE: DNA
<213> ORGANISM: Artificial Sequence

```
<220> FEATURE:
<223> OTHER INFORMATION: Primer

<400> SEQUENCE: 14
tcgtggctgt tgcgtagg                                                   18

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
tgcgccctcc gtatcttac                                                  19

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
atcttagagg ccacgaacat gc                                              22

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
cagcctactg gagatcagga tga                                             23

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ggagtccttg gatgagtctc ga                                              22

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
gcgaactcac acaggcgaga aacc                                            24

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tcgcttcctc ttcctccgac aca                                             23
```

```
<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
cccattgccc ctgctcctg                                                  19

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
tgtgtccgcc ggtgtctgg                                                  19

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
caattacggg gtcattagtt catagc                                          26

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
atacgtagat gtactgccaa gtagga                                          26

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cttcctgcca caatgtcaca g                                               21

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
cctttctcat gcttgcttct ctg                                             23
```

TELOMERASE REVERSE TRANSCRIPTASE-BASED THERAPIES

This application is a National Stage application of PCT/EP2015/067874, filed 4 Aug. 2015, which claims priority to European Patent Application No. 14382312.8, filed 8 Aug. 2014, the contents of all of which are hereby incorporated by reference in their entireties.

FIELD OF INVENTION

This invention falls within the field of molecular biology, biotechnology and medicine. More particularly, it relates to compositions and methods useful for the treatment of conditions associated with short telomere length. More particularly, it relates to compositions and methods useful for the treatment of conditions associated with aplastic anemia.

BACKGROUND OF THE INVENTION

Telomeres are specialized structures at the ends of chromosomes, which have a role in protecting the chromosome ends from DNA repair and degrading activities (Blackburn, 2001. Cell 106, 661-673; de Lange, 2005. Genes Dev. 19, 2100-2110). Mammalian telomeres consist of TTAGGG repeats bound by a multi-protein complex known as shelterin (de Lange, 2005. Genes Dev. 19, 2100-2110). A minimum length of TTAGGG repeats and the integrity of the shelterin complex are necessary for telomere protection (Blackburn, 2001. Cell 106, 661-673; de Lange, 2005. Genes Dev. 19, 2100-2110). Telomerase is a cellular reverse transcriptase (TERT, telomerase reverse transcriptase; also known as TP2; TRT; EST2; TCS1; hEST2) capable of compensating telomere attrition through de novo addition of TTAGGG repeats onto the chromosome ends by using an associated R A component as template (Terc, telomerase RNA component) (Greider and Blackburn, 1985. Cell 43, 405-413). Telomerase is expressed in most adult stem cell compartments, however, this is not sufficient to maintain telomere length as evidenced by the fact that telomere shortening occurs with age in most human and mouse tissues (Harley et al., 1990. Nature 345, 458-460; Blasco, 2007. Nat Chem Biol. 3, 640-649; Flores et al, 2008. Genes and Dev 22, 654-667).

Mice carrying homozygous deletion for the TERC gene (the telomerase RNA component) lack any detectable telomerase activity and showed progressive telomere shortening from one generation to the other at a rate comparable to the rate reported in human cells (Blasco et al., 1997). Severe phenotypes typical of late generation TERC−/−mice (e.g. bone marrow aplasia and signs of premature aging) could be rescued by re-introducing a copy of the TERC gene (Samper et al., 2001). Multiple tissue degeneration arising in later generations in a conditional mouse model defective for TERT (the catalytic telomerase subunit) could be reversed upon telomerase reactivation even in aged mice (Jaskelioff et al., 2011).

In the context of wild-type mice, introducing an additional copy of the telomerase gene, which is expressed in a wide range of epithelial tissues, led to an increased wound healing capacity of the skin (Gonzalez-Suarez et al., 2001). When this allele was introduced in a tumour-resistant genetic background (Sp53/Sp16/SArf) remarkable delay of aging in concert with an increased median lifespan of 40% compared to mice not expressing the telomerase transgene was observed (Tomas-Loba et al., 2008).

A virus (AAV) based telomerase gene therapy was found to be beneficial to extend health span, in the context of normal physiological aging in wild-type mice. In the study examining this benefit, adult and aged mice were subjected to AAV9-mTERT gene therapy to broadly express the catalytic subunit of mouse telomerase (mTERT). The health span of the TERT treated mice was significantly increased, and aging was decelerated, as indicated by a number of physiological parameters (glucose and insulin tolerance, osteoporosis, neuromuscular coordination, rota-rod, etc). In addition, their mean lifespan, compared to control groups, was increased by 24% and 13% in adult an old mice, respectively. A single intravenous administration of AAV9-TERT in adult mice resulted in an increase in telomere length in peripheral blood cells (Bernardes de Jesus et al., 2012).

Shortened telomeres have been associated with numerous diseases, such as Dyskeratosis congenita, Aplastic anaemia, Myelodysplastic Syndrome, and Fanconi anaemia. Given the severity of these diseases and the poor prognosis of the patients suffering from them, there is a need for novel therapies to treat diseases associated with short telomere length.

Aplastic anemia is a potentially life-threatening, rare and heterogeneous disorder of the blood in which the bone marrow cannot produce sufficiently enough new blood cells due to a marked reduction of immature hematopoietic stem (HSC) and progenitor cells (Scopes et al., 1994, Maciejewski et al., 1994). Accordingly, the main disease manifestations are pancytopenia and marrow hypoplasia which can emerge at any stage of life but are more frequent in young people (age 10-25 years) and the elderly (>60 years) (Marsh et al., 2009). Aplastic anemia can be acquired or inherited. The acquired type is mainly autoimmune-mediated but can also be triggered by environmental factors such as radiation, toxin and virus exposure (Nakao, 1997). The congenital form is rarer, however, mutations in more than 30 genes with functions in DNA repair, ribosome biogenesis and telomere maintenance pathways have been identified to date (Dokal & Vulliamy, 2010). A frequently observed clinical feature of aplastic anemia is short telomere length in peripheral blood leukocytes even in the absence of mutations in the telomere maintenance machinery.

Telomeres, the termini of vertebrate chromosomes are highly specialised nucleoprotein structures composed of hexanucleotide (TTAGGG) tandem repeat sequences which are bound by a six protein complex (TRF1, TRF2, TIN2, RAP1, TPP1 and POT1) termed shelterin (Blackburn, 2001, de Lange, 2005). These structures are essential for chromosome integrity by preventing telomere fusions and telomere fragility. Telomere length is controlled by the ribonucleoprotein enzyme telomerase which can de novo add telomeric sequences onto telomeres. Because telomeric sequence is naturally lost upon every cell division (known as the end replication problem) and somatic cells express telomerase at very low levels or not at all telomeres shorten throughout life. When telomeres become critically short they lose their protective function and a persistent DNA damage response at the telomeres is triggered which subsequently leads to a cellular senescence response (Harley et al., 1990, Flores et al., 2008). HSCs, in contrast to most somatic cells, show low level of telomerase activity. However, this activity is insufficient to stop telomere attrition and consequently the regeneration potential of HSCs cells may become limited during the aging process (Hiyama & Hiyama, 2007). In line with this, recipients of bone marrow transplants have shorter telomere lengths than their donors suggesting that telomerase cannot cope with increased replicative proliferation demand during the engraftment phase (Wynn et al., 1998). Moreover, telomeres have been shown to shorten much faster in patients with aplastic anemia compared to the normal aging-related attrition found in healthy individuals potentially owed to a higher than normal number of cell divisions (Ball et al., 1998).

Accelerated telomere shortening due to defects in telomere components or telomerase itself prematurely limits the proliferation potential of cells which particularly affects the tissue renewal capacity in stem cell compartments (Harley et al., 1990, Flores et al., 2005). Thus, tissues with a high proliferative index such as the hematopoietic system are particularly affected by lower than normal telomerase levels which can ultimately lead to severe disorders such as aplastic anemia (Vulliamy et al., 2002). For instance, the telomeropathy dyskeratosis congenita has been linked to mutations in 7 genes with important functions in telomere maintenance (TERT, TERC, DKC1, TIN2, NOP10, NHP2 and TCAB1) and is characterized by very short telomeres. Dyskeratosis congenita is a multisystem syndrome comprising diverse clinical features such as nail dystrophy, oral leucoplakia, abnormal skin pigmentation and cerebellar hypoplasia (Dokal, 2011). The most severe complication, however, is the development of aplastic anemia in 80% of the cases underlining that the clinical features are caused by excessive telomere shortening which eventually leads to the exhaustion of the stem cell reserve (Dokal & Vulliamy, 2010).

The causality between proliferation potential and telomere length suggests that a therapeutic intervention with telomerase, aimed at preventing telomere loss beyond a critically short length, may be a feasible strategy to treat those forms of aplastic anemia associated with limited blood forming capacity due to the presence of short telomeres. In this regard, we previously developed a telomerase (Tert) gene therapy using adeno-associated virus (AAV9) vectors. Interestingly, telomerase gene therapy using AAV9 Tert in adult wilt-type mice attenuated or reverted the aging-associated telomere erosion in peripheral blood monocytes (Bernardes de Jesus et al., 2012), suggesting that this gene therapy may be effective in the treatment of hematological disorders related to short telomeres.

To test this hypothesis we used our recently generated mouse model of aplastic anemia which recapitulates the bone marrow phenotype observed in patients (Beier et al., 2012). In this mouse model bone marrow specific depletion of the shelterin gene Trf1 cause severe telomere uncapping and provokes a DNA damage response which in turn leads to a fast clearance of those HSCs and progenitor cells deficient for Trf1. However, in this model we induce Trf1 deletion at a frequency that does not target 100% of the HSCs and progenitor cells. Therefore, cells that retain intact Trf1 undergo additional rounds of compensatory proliferation leading to fast telomere attrition. Thus, partial depletion of the stem and progenitor cell compartment by Trf1 deletion recapitulates the compensatory hyperproliferation observed after bone marrow transplantation or in autoimmune-mediated aplastic anemia, as well as presence of very short telomeres in patients owing to mutations in telomere maintenance genes. Interestingly, in our mouse model we can adjust the rate of telomere shortening through the frequency of Trf1 deletion-mediated HSC depletion which allows to control the onset of bone marrow aplasia and pancytopenia (Beier et al., 2012).

In this study we employ this mouse model of aplastic anemia to investigate whether telomerase activation using state of the art gene therapy vectors can be an effective treatment to attenuate telomere attrition and HSC depletion, and thus prevent bone marrow failure.

SUMMARY

The invention provides compositions and methods useful for the treatment and prevention of conditions associated with short telomere length.

One aspect of the invention provides a method of treating a patient with a condition associated with short telomere length comprising administering to the patient a nucleic acid vector comprising a coding sequence for telomerase reverse transcriptase (TERT). In one embodiment, the TERT is encoded by a nucleic acid sequence comprising a sequence that is at least 90% identical to the sequence of SEQ ID NO: 1 or SEQ ID NO: 3. In one embodiment, the TERT is encoded by a nucleic acid sequence comprising the sequence of SEQ ID NO: 1 or SEQ ID NO: 3. In one embodiment, the TERT is encoded by a nucleic acid sequence consisting of the sequence of SEQ ID NO: 1 or SEQ ID NO: 3 In one embodiment, the TERT comprises an amino acid sequence that is at least 90% identical to the amino acid sequence of SEQ ID NO:2 or SEQ ID NO: 4. In one embodiment, the TERT comprises an amino acid sequence of SEQ ID NO:2 or SEQ ID NO: 4. In one embodiment, the TERT consists of the amino acid sequence of SEQ ID NO:2 or SEQ ID NO: 4. In one embodiment, the nucleic acid sequence encoding TERT is operably linked to a regulatory sequence that drives the expression of the coding sequence. In one embodiment, the vector is a non-integrative vector, such as an adeno-associated virus-based non-integrative vector. In one embodiment, the vector is an adeno-associated virus-based vector derived from a serotype 9 adeno-associated virus (AAV9). In one embodiment, the capsid of the adeno-associated virus-based vector is made of capsid proteins of the serotype 9 adeno-associated virus (AAV9), and the nucleic acid sequence contained in the capsid is flanked at both ends by internal terminal repeats corresponding to serotype 2 adenoassociated viruses. In one embodiment, the nucleic acid contained in the capsid comprises a fragment which encodes the amino acid sequence coding for TERT. In one embodiment, the vector comprises a regulatory sequence which is a constitutive promoter. In one embodiment, the regulatory sequence is the cytomegalovirus (CMV) promoter. In one embodiment, the condition associated with short telomere length is characterized by mutations in a gene or genes involved in telomere maintenance. In one embodiment, the condition associated with short telomere length is selected from the group consisting of Dyskeratosis congenita, Aplastic anaemia, Myelodysplastic Syndrome, Fanconi anaemia.

In yet further embodiments, the invention is directed to the following set of subject matters:

1. A method of treating a patient with a condition associated with short telomere length comprising administering to the patient a nucleic acid vector comprising a coding sequence for telomerase reverse transcriptase (TERT).

2. The method of 1, wherein TERT is encoded by a nucleic acid sequence comprising a sequence that is at least 90% identical to the sequence of SEQ ID NO: 1 or SEQ ID NO: 3.

3. The method of 1 or 2, wherein TERT is encoded by a nucleic acid sequence comprising the sequence of SEQ ID NO: 1 or SEQ ID NO: 3.

4. The method of any of 1-3, wherein TERT is encoded by a nucleic acid sequence consisting of the sequence of SEQ ID NO: 1 or SEQ ID NO: 3

5. The method of any of 1-4, wherein TERT comprises an amino acid sequence that is at least 90% identical to the amino acid sequence of SEQ ID NO:2 or SEQ ID NO: 4.

6. The method of any of 1-5, wherein TERT comprises an amino acid sequence of SEQ ID NO:2 or SEQ ID NO: 4.

7. The method of any of 1-6, wherein TERT consists of the amino acid sequence of SEQ ID NO:2 or SEQ ID NO: 4.

8. The method of any of 1-7, wherein the nucleic acid sequence encoding TERT is operably linked to a regulatory sequence that drives the expression of the coding sequence.

9. The method of any of 1-8, wherein the vector is a non-integrative vector.

10. The method of any of 1-9, wherein the vector is an adeno-associated virus-based non-integrative vector.

11. The method of any of 1-10, wherein the vector is an adeno-associated virus-based vector derived from a serotype 9 adeno-associated virus (AAV9).

12. The method of 11, wherein the capsid of the adeno-associated virus-based vector is made of capsid proteins of the serotype 9 adeno-associated virus (AAV9), and the nucleic acid sequence contained in the capsid is flanked at both ends by internal terminal repeats corresponding to serotype 2 adenoassociated viruses.

13. The method of 12, wherein the nucleic acid contained in the capsid comprises a fragment which encodes the amino acid sequence coding for TERT.

14. The method of any of 1-13, wherein the vector comprises a regulatory sequence which is a constitutive promoter.

15. The method of 14, wherein the regulatory sequence is the cytomegalovirus (CMV) promoter.

16. The method of any of 1-15, wherein the condition associated with short telomere length is characterized by mutations in a gene or genes involved in telomere maintenance.

17. The method of any of 1-16, wherein the condition associated with short telomere length is selected from the group consisting of Dyskeratosis congenita, Aplastic anaemia, Myelodysplastic Syndrome, Fanconi anaemia, and pulmonary fibrosis.

18. A nucleic acid vector comprising a coding sequence for telomerase reverse transcriptase (TERT) for use in treating a condition associated with short telomere length.

19. The nucleic acid vector of 18, wherein TERT is encoded by a nucleic acid sequence comprising a sequence that is at least 90% identical to the sequence of SEQ ID NO: 1 or SEQ ID NO: 3.

20. The nucleic acid vector of 18 or 19, wherein TERT is encoded by a nucleic acid sequence comprising the sequence of SEQ ID NO: 1 or SEQ ID NO: 3.

21. The nucleic acid vector of any of 18-20, wherein TERT is encoded by a nucleic acid sequence consisting of the sequence of SEQ ID NO: 1 or SEQ ID NO: 3

22. The nucleic acid vector of any of 18-21, wherein TERT comprises an amino acid sequence that is at least 90% identical to the amino acid sequence of SEQ ID NO:2 or SEQ ID NO: 4.

23. The nucleic acid vector of any of 18-22, wherein TERT comprises an amino acid sequence of SEQ ID NO:2 or SEQ ID NO: 4.

24. The nucleic acid vector of any of 18-23, wherein TERT consists of the amino acid sequence of SEQ ID NO:2 or SEQ ID NO: 4.

25. The nucleic acid vector of any of 18-24, wherein the nucleic acid sequence encoding TERT is operably linked to a regulatory sequence that drives the expression of the coding sequence.

26. The nucleic acid vector of any of 18-25, wherein the vector is a non-integrative vector.

27. The nucleic acid vector of any of 18-26, wherein the vector is an adeno-associated virus-based non-integrative vector.

28. The nucleic acid vector of any of 18-27, wherein the vector is an adeno-associated virus-based vector derived from a serotype 9 adeno-associated virus (AAV9).

29. The nucleic acid vector of 28, wherein the capsid of the adeno-associated virus-based vector is made of capsid proteins of the serotype 9 adeno-associated virus (AAV9), and the nucleic acid sequence contained in the capsid is flanked at both ends by internal terminal repeats corresponding to serotype 2 adenoassociated viruses.

30. The nucleic acid vector of 29, wherein the nucleic acid contained in the capsid comprises a fragment which encodes the amino acid sequence coding for TERT.

31. The nucleic acid vector of any of 18-30, wherein the vector comprises a regulatory sequence which is a constitutive promoter.

32. The nucleic acid vector of 31, wherein the regulatory sequence is the cytomegalovirus (CMV) promoter.

33. The nucleic acid vector of any of 18-32, wherein the condition associated with short telomere length is characterized by mutations in a gene or genes involved in telomere maintenance.

34. The nucleic acid vector of any of 18-33, wherein the condition associated with short telomere length is selected from the group consisting of Dyskeratosis congenita, Aplastic anaemia, Myelodysplastic Syndrome, Fanconi anaemia, and pulmonary fibrosis.

35. The nucleic acid vector of any of 18-34, wherein the condition associated with short telomere length is dyskeratosis congenita.

DETAILED DESCRIPTION OF EMBODIMENTS OF THE INVENTION

Figure 1:
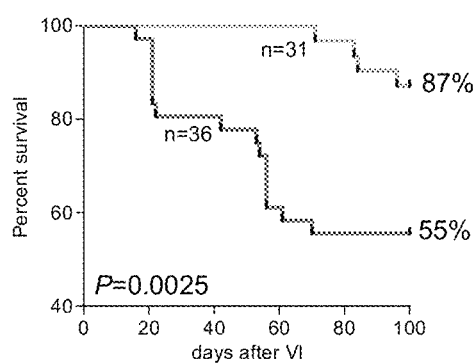
FIG. 1: AAV9-Tert effects on survival (A-C) and blood counts (D-E)
Figure 1:
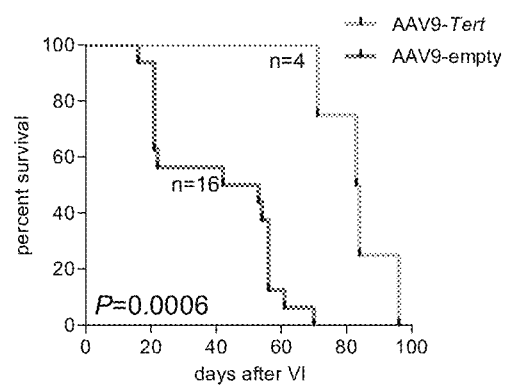
Figure 1:
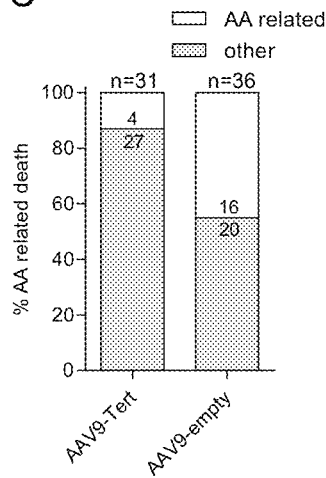
Figure 1:
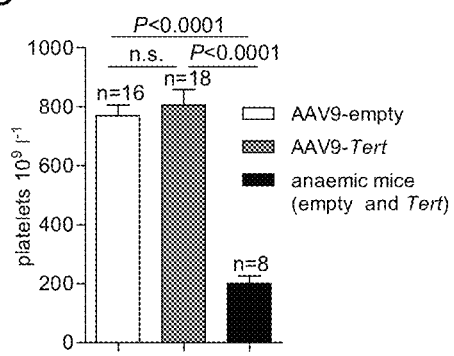
Figure 1:
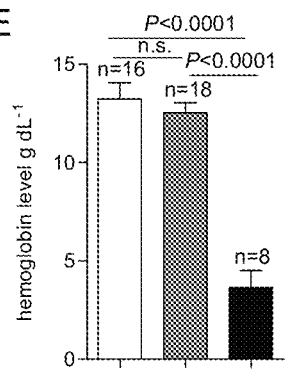

The invention provides compositions and methods useful for the treatment and prevention of conditions associated with short telomere length.

A "condition associated with short telomere length" is one which is characterized by an accumulation of critically short telomeres. In certain embodiments, subjects suffering from such a condition exhibit premature onset of pathologies resulting from a defective regenerative capacity of tissues.

In certain embodiments, the condition associated with short telomere length is characterized by mutations in a gene or genes involved in telomere maintenance. Specific examples of such genetically based conditions include, but are not limited to Dyskeratosis congenita, Aplastic anaemia, Myelodysplastic Syndrome, Fanconi anaemia, and pulmonary fibrosis.

Dyskeratosis congenita (DKC) is a genetically heterogeneous human disease, which is paradigmatic of premature ageing syndromes (Dokal, 2011). DKC is characterised by the presence of short/dysfunctional telomeres owing to mutations in genes related to telomere maintenance, being the most frequently mutated those encoding proteins of the telomerase complex (i.e. TERT, TERC, NOP10, DKC1, NHP2) (Dokal, 2011; Dokal and Vulliamy, 2010; Mason and Bessler, 2011; Savage and Alter, 2008). In addition, a subset of patients carry mutations in the gene encoding TIN2 (TRF1-interacting protein) a component of the shelterin complex, which binds and protects mammalian telomeres (Dokal, 2011; Martinez and Blasco, 2011; Walne et al., 2008). Both a functional telomerase complex and a proper telomere capping structure by the shelterin proteins are required for maintenance and capping of chromosome ends, respectively.

Clinical features of patients suffering from DKC include skin abnormalities (i.e. skin hyperpigmentation), signs of premature aging (i.e. hair greying, nail dystrophy, oral leucoplakia, etc), predisposition to cancer, and several other life-threatening conditions, including aplastic anemia and pulmonary fibrosis (Armanios and Blackburn, 2012). In particular, tissues with a high proliferative index are most affected due to the loss of telomeric DNA that occurs upon each cell division. This explains why DKC patients are particularly vulnerable to impaired bone marrow function leading to pancytopenia and eventually bone marrow failure (BMF) (Armanios and Blackburn, 2012; Blasco, 2007)

Aplastic anaemia, is a life threatening bone marrow disorder characterised by hypocellular bone marrow and low blood cell counts. Patients with acquired aplastic anaemia present with leukocytes which have considerably shorter telomeres than age-matched healthy individuals (Carroll and Ly, 2009). Aplastic anaemia is frequently caused by an autoimmune mediated attack against hematopoietic stem cells. However, recent studies demonstrated that mutations in the core telomerase components TERT and TERC are the underlying cause in a clinically relevant subpopulation (Yamaguchi et al., 2003; Yamaguchi et al., 2005). Mutations in the core telomerase components TERT and TERC, as well as in the shelterin component TIN2 have been linked to this disease (Savage et al., 2006).

Myelodysplastic Syndrome (MDS) encompasses several bone marrow diseases characterised by ineffective production of the myeloid class of blood cells. Caused by progressive bone marrow failure, similar to DKC, MDS patients often report with severe anaemia and cytopenias. In approximately one third of the cases the disease progresses quickly and transforms into acute myelogenous leukemia (AML) which is particularly resistant to treatment. Even though shortened telomeres in patients with MDS suggest that insufficient or hampered telomeric maintenance is causative for the syndrome, only 3 out of 210 cases showed heterozygous TERC mutations in a previous study (Yamaguchi et al., 2003). However, a recently published study clearly circumstantiated the connection between human telomerase mutations and MDS, aplastic anaemia and AML. (Holme et al., 2012) reported various families with mutations of the telomerase components TERC and TERT which e.g. the grandfather suffered from AML, the daughter from MDS and the grandson from aplastic anaemia (Holme et al., 2012) emphasising the close relation of different clinical manifestations with impaired telomere maintenance.

Fanconi anaemia (FA) is a heterogeneous genetic disease caused by mutations in genes involved in DNA repair. Affected individuals display multiple congenital defects and haematological deficiencies at a young age of onset (Kee and D'Andrea, 2012). Manifestations related to the latter however are the predominant symptoms of this syndrome and as the disease progresses can develop into the aforementioned syndromes including aplastic anaemia, MDS and AML. Importantly, patients suffering from FA have been also shown to present shorter telomeres than normal (Gadalla et al., 2010). The facts that mutations causing FA show impaired DNA damage response (DDR) and telomeres are particularly vulnerable to replicative stress may provide an explanation for the observed telomere erosion. In support of this Callen et al. (2002) suggested that in FA patients increased telomere breakage in concert with replicative shortening account for the observed telomere shortening.

Pulmonary fibrosis refers to a condition characterised by scarring of the lung tissue. Pulmonary fibrosis can be caused by many factors, including chronic inflammatory processes, infections, environmental compounds, ionizing radiation (for example radiation therapy to treat tumors of the chest), chronic medical conditions (lupus, rheumatoid arthritis). Idiopathic pulmonary fibrosis (IPF) refers to pulmonary fibrosis without an identifiable cause.

Accordingly, the invention provides methods of treating a patient suffering from a condition associated with short telomere length comprising administering to the patient an agent which increases the telomere length of the patient. In one embodiment, the agent prevents degradation of the chromosomal ends. In one embodiment, the agent increases the activity of telomerase reverse transcriptase (TERT). In one embodiment, the method of treatment is a gene therapy method comprises administering to the patient a nucleic acid vector comprising a coding sequence for telomerase reverse transcriptase (TERT).

In certain embodiments, the TERT sequence used in the gene therapy vector is derived from the same species as the subject. For example, gene therapy in humans would be carried out using the human TERT sequence. Gene therapy in mice would be carried out using the mouse TERT sequence, as described in the examples. In one embodiment, the TERT is encoded by the nucleic acid sequence as set forth in SEQ ID NO: 1 or SEQ ID NO: 3 (human TERT variants 1 and 2), or is an active fragment or functional equivalent of SEQ ID NO: 1 or SEQ ID NO: 3. The polypeptide sequence encoded by SEQ ID NO: 1 is set forth in SEQ ID NO: 2. The polypeptide encoded by SEQ ID NO: 3 is set forth in SEQ ID NO: 4. As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to TERT encoded by SEQ ID NO: 1 or SEQ ID NO: 3. Functional equivalents may be artificial or naturally-occurring. For example, naturally-occurring variants of the TERT sequence in a population fall within the scope of functional equivalent. TERT sequences derived from other species also fall within the scope of the term "functional equivalent", in particular the murine TERT sequence given in SEQ ID NO: 5. In a particular embodiment, the functional equivalent is a nucleic acid with a nucleotide sequence having at least 75%, 80%>, 85%, 90%, 95%, 96%, 97%, 98%, 99%, 99.5%, 99.9% identity to SEQ ID NO: 1 or SEQ ID NO: 3. In a further embodiment, the functional equivalent is a polypeptide with an amino acid sequence having at least 75%, 80%, 85%, 90%, 95%, 96%, 97%, 98%, 99%, 99.5%, 99.9% identity to SEQ ID NO: 2 or SEQ ID NO: 4. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to SEQ ID NO: 1 or SEQ ID NO: 3. The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the sequence as set forth in SEQ ID NO:2 or SEQ ID NO: 4, but that show little homology to the nucleic acid sequence given in SEQ ID NO: 1 or SEQ ID NO: 3 because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in SEQ ID NO: 1 or SEQ ID NO: 3 or the amino acid sequence as set forth in SEQ ID NO: 2 or SEQ ID NO: 4. An active fragment may be of any size provided that TERT activity is retained. A fragment will have at least 75%, 80%, 85%, 90%, 95%, 96%, 97%, 98%, 99%, 99.5%, 100% identity to SEQ ID NO: 1-4 along the length of the alignment between the shorter fragment and SEQ ID NO: 1-4.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity.

Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and FASTA (Lipman, D J; Pearson, W R (1985). "Rapid and sensitive protein similarity searches". Science 227 (4693): 1435-41; http://fasta.bioch.Virginia, edu/fasta_www2/fasta_list2.shtml) and variations on these alignment programs.

In one embodiment, the method of treatment is a gene therapy method and/or the nucleic acid vector used is a gene therapy vector. Gene therapy methods and vectors are well known in the art and generally comprise delivering a nucleic acid encoding a therapeutically active protein to a subject. The nucleic acid may be delivered in a number of ways including delivering naked DNA such as plasmid or minicircles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. Suitable inducible expression systems are known in the art and include the CRE-LOX recombinase based system which is suitable for use in mice and tetracycline-regulated which can be used in the treatment of human subjects.

In one embodiment the gene therapy vector is a viral vector. Viral gene therapy vectors are well known in the art. Vectors include integrative and non-integrative vectors such as those based on retroviruses, adenoviruses (AdV), adeno-associated viruses (AAV), lentiviruses, pox viruses, alphaviruses, and herpes viruses.

Using non-integrative viral vectors, such as AAV, seems to be particularly advantageous. In one aspect, this is because non-integrative vectors do not cause any permanent genetic modification. Second, the vectors target to adult tissues, avoiding having the subjects under the effect of constitutive telomerase expression from early stages of development. Additionally, non-integrative vectors effectively incorporate a safety mechanism to avoid over-proliferation of TERT expressing cells. Cells will lose the vector (and, as a consequence, the telomerase expression) if they start proliferating quickly.

Particular examples of suitable non-integrative vectors include those based on adenoviruses (AdV) in particular gutless adenoviruses, adeno-associated viruses (AAV), integrase deficient lentiviruses, pox viruses, alphaviruses, and herpes viruses. Preferably, the non-integrative vector used in the invention is an adeno-associated virus-based non-integrative vector, similar to natural adeno-associated virus particles. AAV preferentially targets post-mitotic tissues, which are considered more resistant to cancer than the highly proliferative ones. Examples of adeno-associated virus-based non integrative vectors include vectors based on any AAV serotype, i.e. AAV1, AAV2, AAV3, AAV4, AAV5, AAV6, AAV7, AAV8, AAV9, AAV10, AAV11 and pseudotyped AAV. Tissue specificity is determined by the capsid serotype. Pseudotyping of AAV vectors and capsid engineering to alter their tropism range will likely be important to their use in therapy.

Vectors derived from adeno-associated viruses (AAVs) have emerged as one of the vectors of choice for many gene transfer applications because of their many desirable properties, including capability to transduce a broad range of tissues at high efficiency, poor immunogenicity and an excellent safety profile (Merten, Geny-Fiamma et al. 2005; Buning, Perabo et al. 2008), toxicity being absent in many preclinical models (Niemeyer, Herzog et al Blood 2009; Mas, Montane et al Diabetes 2006; Jiang, Lillicrap et al blood 2006; Ghosh, Yue et al Molecular therapy 2007; Tafuro, Ayuso et al cardiovascular research 2009). AAV vectors transduce post-mitotic cells and can sustain long-term gene expression (up to several years) both in small and large animal models of disease (Niemeyer, Herzog et al Blood 2009; Mas, Montane et al Diabetes 2006; Jiang, Lillicrap et al blood 2006; Ghosh, Yue et al Molecular therapy 2007; Tafuro, Ayuso et al cardiovascular research 2009). Safety and efficacy of AAV gene transfer has been extensively studied in humans with encouraging results in the liver, muscle, CNS, and retina (Manno et al Nat medicine 2006, Stroes et al ATVB 2008, Kaplitt, Feigin, Lancet 2009; Maguire, Simonelli et al NEJM 2008; Bainbridge et al NEJM 2008).

AAV2 is the best characterized serotype for gene transfer studies both in humans and experimental models. AAV2 presents natural tropism towards skeletal muscles, neurons, vascular smooth muscle cells and hepatocytes. AAV2 is therefore a good choice of vector to target these tissues, in particular when using the methods or vectors of the invention to treat a condition associated with one of these tissues. For example, treatment of neuromuscular degeneration may be targeted to skeletal muscle and/or neurons in this way.

Newly isolated serotypes, such as AAV7, AAV8, and AAV9 have been successfully adopted in preclinical studies (Gao, Alvira et al PNAS 2002). Although limited immunologic responses have been detected in human subjects treated with AAV2 or AAV1 against the AAV capsid (Manno et al Nat Med 2006; Mingozzi et al Nat Med 2007; Brantly et al PNAS 2009; Mingozzi et al blood 2009), long term expression of the therapeutic gene is possible depending on the target tissue and the route of administration (Brantly et al PNAS 2009; Simonelli et al mol therapy 2010). In addition, the use of non-human serotypes, like AAV8 and AAV9, might be useful to overcome these immunological responses in subjects, and clinical trials have just commenced (ClinicalTrials.gov Identifier: NCT00979238).

Altogether, these encouraging data suggest that AAV vectors are useful tools to treat human diseases with a high safety and efficient profile.

The choice of adeno-associated viruses of wide tropism, such as those derived from serotype 9 adeno-associated virus (AAV9) is particularly advantageous when treating conditions associated with short telomere length. AAV9 viruses have shown efficient transduction in a broad range of tissues, with high tropism for liver, heart and skeletal muscle (Inagaki et al Molecular Therapy 2006) and thus the beneficial effects of gene therapy can be achieved in more tissues. In addition, AAV9 vectors have the unique ability to cross the blood-brain-barrier and target the brain upon intravenous injection in adult mice and cats (Foust et al Nature biotechnology 2009; Duque et al Molecular therapy et al 2009).

One aspect of the invention provides a system in which the capsid (which is the part of the virus which determines the virus tropism) of the adeno-associated virus-based vector is made of capsid proteins of the serotype 9 adeno-associated virus (AAV9). In one embodiment of the viral vectors for use in the invention, the polynucleotide sequence packed in the capsid is flanked by internal terminal repeats (ITRs) of an adeno-associated virus, preferably of serotype 2 which has been extensively characterised in the art, and presents a coding sequence located between the ITRs. As set out above, the nucleic acid preferably codes for a functional TERT polypeptide. In one embodiment, the regulatory sequence operatively linked to the TERT coding sequence is the cytomegalovirus promoter (CMV), although other suitable regulatory sequences will be known to those of skill in the art.

When treating conditions associated with short telomere length, it is advantageous to target the treatment to the effected tissues. The choice of AAV serotype for the capsid protein of the gene therapy vector may be thus based on the desired site of gene therapy. If the target tissue is skeletal muscle, for example, in treating loss of neuromuscular coordination, AAV1- and AAV6-based viral vectors can be used. Both of these serotypes are more efficient at trans fecting muscle than other AAV serotypes. AAV3 is useful for trans fecting haematopoietic cells. A thorough review of AAV-based vectors for gene therapy can be found in Shi et al, (2008) "AAV-based targeting gene therapy" Am. J. Immunol. 4:51-65.

Alternatively, other viral vectors can be used in the present invention. Any vector compatible with use in gene therapy can be used in the present invention. Heilbronn & Weger (2010) Handb Exp Pharmacol. 197: 143-70 provides a review of viral vectors that are useful in gene therapy. In accordance with all the previous discussion, vectors comprising a coding sequence for telomerase reverse transcriptase (TERT) suitable for use in gene therapy are an important point for putting the invention into practice. Suitable gene therapy vectors include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. Preferably, TERT is encoded by the nucleic acid sequence as set forth in SEQ ID NO: 1 or SEQ ID NO: 3, or is an active fragment or functional equivalent of TERT.

The term gene therapy vector includes within its scope naked DNA molecules such as plasmids or mini-circles, i.e. circular DNA molecules which do not contain bacterial DNA sequences, provided that the TERT coding sequence and its linked regulatory element are inserted in the plasmid, as well as to more complicated systems, such as particles with the structure of virions (viral particles), comprising at least a capsid and at least a polynucleotide sequence, with a size that allows the polynucleotide sequence to be packed within the capsid in a manner similar to that of the native genome of the virus of origin of the capsid. The polynucleotide sequence must include a region where the TERT coding sequence and its linked regulatory element are inserted such that the telomerase reverse transcriptase protein can be expressed from that polynucleotide sequence once the viral particle has infected a cell.

In one embodiment, the gene therapy vector suitable for being used in the invention is a non-integrative vector, such as an adeno-associated virus-based non-integrative vector. For the purposes of the invention, the choice of non-integrative vectors seems to be particularly advantageous, because they do not cause any permanent genetic modification. Also, as stated before, such vectors incorporate a safety mechanism to avoid over-proliferation of TERT expressing cells that will lose the vector if the cells start proliferating quickly.

Adeno-associated virus-based vectors derived from a serotype 9 adeno-associated virus (AAV9) are preferred because the beneficial effects can be achieved in more tissues (see above). In one particularly preferred embodiment, the regulatory sequence operatively linked to the TERT coding sequence is the cytomegalovirus promoter (CMV). The nucleic acid sequence encoding TERT is operably linked to a regulatory sequence that drives the expression of the coding sequence. As used herein, the term "regulatory element" means a nucleic acid sequence that serves as a promoter, i.e., regulates expression of a nucleic acid sequence operably linked to the promoter. Such "regulatory elements" or "promoters" can control the expression of linked nucleic acid sequences either constitutively or inducible.

The regulatory sequence may be a constitutive promoter. An example of a regulatory sequence which is a constitutive promoter is the cytomegalovirus (CMV) promoter.

The expression of TERT following gene therapy according to the invention persists for a time of several months to several years. In mice, TERT expression was detectable after 5 months. In monkey, gene expression following gene therapy with an AAV-based vector has been detected up to 6 years after treatment and up to 8 years in dogs (Rivera et al Blood 2005, and Niemeyer et al blood 2009). Frequent repetition of treatment using the methods and vectors of the invention is therefore not necessary. In one embodiment of the invention, the subject is treated once. In an alternative embodiment, the subject is treated initially, and is then treated again once TERT expression levels decrease by about 50% of those attained immediately following treatment. Treatment may be repeated with the same or alternative vector to maintain the reduction in age-related disorders if necessary, for example annually, or once every 5 years or once a decade. When administering a second or subsequent dose, it may be necessary to use a different gene therapy vector, for example when using an AAV-based vector the second and subsequent administrations may be a vector with a capsid derived from a different serotype than that used for the first administration. It is possible that a subject may develop neutralising antibodies to the first gene therapy vector, making it ineffective if administered a second or subsequent time (Amado et al (2010) Science Translational Medicine 2(21):21ra16).

The methods of treatment of the invention have the effect of treating and/or preventing conditions associated with short telomere length. In a further aspect, therefore, the invention refers to a gene therapy method or the use of a nucleic acid vector as described above, for use in the treatment or prevention in a subject of condition associated with short telomere length, including but not limited to genetically based conditions such as Dyskeratosis congenita, Aplastic anaemia, Myelodysplastic Syndrome, Fanconi anaemia, and pulmonary fibrosis.

The effectiveness of treatment of the conditions associated with short telomere length can be measured by various methods known in the art. In one embodiment, the effectiveness of the treatment is measured by an increase in lifespan of a treated patient suffering from a condition associated with short telomere length as compared to the expected lifespan of an untreated patient suffering from the same condition. In certain embodiments, the lifespan is extended by 5%, 10%, 15%, 20% or more, with reference to the expected lifespan for a patient suffering from the same condition.

In one embodiment, the effectiveness of the treatment is measured by a delayed or prevented bone marrow failure in a treated patient suffering from a condition associated with short telomere as compared to the expected onset of bone marrow failure in an untreated patient suffering from the same condition. In certain embodiments, the delay in the onset of bone marrow failure of a treated patient suffering from a condition associated with short telomere length is extended by 5%, 10%, 15%, 20% or more, with reference to the expected onset of bone marrow failure for an untreated patient suffering from the same condition.

In one embodiment, the effectiveness of the treatment is measured by an increase in overall fitness of a treated patient suffering from a condition associated with short telomere length treated as compared to the overall fitness of an untreated patient suffering from the same condition. Overall fitness can be determined by measuring physical attributes associated with the particular condition. Examples of such physical attributes include skin abnormalities (such as skin hyperpigmentation), premature aging (such as hair greying, nail dystrophy, oral leucoplakia), and anaemic pallor. Dokal, I. 2011. Hematology Am Soc Hematol Educ Program, 480-486. Thus an increase in overall fitness can be determined by a decrease in physical attributes associated with the particular condition exhibited by the treated patient. Overall fitness can also be measure by determining the blood count of the patient. In one embodiment, increased overall fitness is measured by determining the amount of leukocytes, lymphocytes, thrombocytes in a peripheral blood sample. Higher blood count indicates an increased overall fitness. In certain embodiments, the blood count in a treated patient is increased by 5%, 10%, 15%, 20% or more, with reference to the blood count of an untreated patient suffering from the same condition.

The efficacy of the treatment can also be measured by directly determining telomere length in sample taken from the patient. Telomere length can be measured, for example, by using standard hybridization techniques, such as fluorescence in situ hybridization (FISH), Quantitative Fluorescent in situ hybridization (Q-FISH), or High Throughput Quantitative Fluorescent in situ hybridization (HT Q-FISH). (Gonzalez-Suarez, Samper et al. 2001) in a sample taken from the patient, Samples suitable for telomere analysis include bone marrow tissue and blood samples. Telomere length can also be measured as described in Slagboom et al or Canela et al. (2007, PNAS 104:5300-5305).

In a particular embodiment, samples are taken from the patient undergoing treatment throughout the course of the treatment so that both absolute telomere length and the rate of telomere shortening over the course of treatment can be determined. Samples may be taken every day during the course of treatment, or at longer intervals. In one embodiment, samples are taken once a week, once every two week, once every three weeks, once every 4 weeks, once every five weeks, once every six weeks or longer.

Comparison of telomere length can be measured by a comparing the proportion of short telomeres in a sample taken from a patient. In one embodiment, the proportion of short telomeres is the fraction of telomeres presenting an intensity below the mean intensity of the sample as measured by a in situ hybridization technique, such as FISH or Q-FISH. In embodiment, the proportion of short telomeres is the fraction of telomeres presenting an intensity 75%, 70%, 65%, 60%, 55%, 50%, 45%, 40% or more below the mean intensity of the sample. In one particular embodiment, the proportion of short telomeres is the fraction of telomeres presenting an intensity 50% or more below the mean intensity of the sample.

In another embodiments, the proportion of short telomeres is the fraction of telomeres below a certain length, e.g. 8 kb, 7 kb, 6 kb, 5 kb, or shorter In one embodiment, the proportion of short telomeres is the fraction of telomeres 8 kb or shorter. In another embodiment, the proportion of short telomeres is the fraction of telomeres 7 kb or shorter. In another embodiment, the proportion of short telomeres is the fraction of telomeres 6 kb or shorter. In another embodiment, the proportion of short telomeres is the fraction of telomeres 5 kb or shorter. In another embodiment, the proportion of short telomeres is the fraction of telomeres 4 kb or shorter. In another embodiment, the proportion of short telomeres is the fraction of telomeres 3 kb or shorter.

In one embodiment, the effectiveness of the treatment is measured by a decrease in the proportion of short telomeres in sample taken from a treated patient suffering from a condition associated with short telomere length as compared to a control sample. In one embodiment, the proportion of short telomeres in a sample taken from a treated patient is decreased by 10%, 20%, 30%, 40%, 50%, 60%, 70%, or greater as compared to a control sample. In one embodiment, the control sample is a sample taken from the same patient prior to the treatment, or taken at an earlier stage of the treatment. In another embodiment, the control sample is a sample taken from a patient suffering from the same condition and not provided the treatment.

In a further aspect, the invention is applied to the subject by administering a pharmaceutical composition comprising an effective amount of any one of the gene therapy vectors compatible with the invention described above.

A "pharmaceutical composition" is intended to include the combination of an active agent with a carrier, inert or active, making the composition suitable for diagnostic or therapeutic use in vitro, in vivo or ex vivo.

"Composition" is intended to mean a combination of active agent and another compound or composition, inert (for example, a detectable agent or label) or active. An "effective amount" is an amount sufficient to effect beneficial or desired results. An effective amount can be administered in one or more administrations, applications or dosages.

They will usually include components in addition to the active component (such as the gene therapy vector) e.g. they typically include one or more pharmaceutical carrier(s) and/or excipient(s). A thorough discussion of such components is available in Gennaro (2000) Remington: The Science and Practice of Pharmacy. 20th edition, ISBN: 0683306472.

Compositions will generally be administered to a subject in aqueous form. Prior to administration, however, the composition may have been in a non-aqueous form. For instance, although some viral vectors are manufactured in aqueous form, then filled and distributed and administered also in aqueous form, other viral vectors are lyophilised during manufacture and are reconstituted into an aqueous form at the time of use. Thus a composition of the invention may be dried, such as a lyophilised formulation. The composition may include preservatives such as thiomersal or 2-phenoxyethanol. It is preferred, however, that the composition should be substantially free from (i.e. less than 5 μg/m ĩ ) mercurial material e.g. thiomersal-free.

To control tonicity, it is preferred to include a physiological salt, such as a sodium salt. Sodium chloride (NaCl) is preferred, which may be present at between 1 and 20 mg/ml e.g. about 10+2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The composition may include material for a single administration, or may include material for multiple administrations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Compositions of the invention for use in humans are typically administered in a dosage volume of about 0.5 ml, although a half dose (i.e. about 0.25 ml) may be administered to children.

As well as methods of treatment described herein, the invention also provides a nucleic acid sequence encoding a TERT for use in therapy. The invention also provides a nucleic acid vector comprising a coding sequence for telomerase reverse transcriptase (TERT), for use in a method of therapy and a gene therapy vector comprising a coding sequence for telomerase reverse transcriptase (TERT), for use in a method of therapy. In particular, the therapy may be treating or preventing a condition associated with short telomere length. As described for methods of treatment, the TERT nucleic acid sequence may be the sequence as recited in SEQ ID NO: 1 or SEQ ID NO: 3 or a fragment or functional equivalent thereof. The TERT protein may have a sequence as recited in SEQ ID NO: 2 or SEQ ID NO: 4, or a fragment or functional equivalent thereof.

The term "patient" refers to a mammal. In certain embodiments the patient is a rodent, primate, ungulate, cat, dog, or other domestic pet or domesticated mammal. In certain embodiments, the mammal is a mouse, rat, rabbit, pig, horse, sheep, cow, domestic cat or dog, or a human. In a preferred embodiment, the patient is a human.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

EXAMPLES

Example 1

Mouse Model for Dyskeratosis Congenita

Mice of C57B6 background that are homozygous carrier of a conditional TRF1 transgene (TRF1$^{flox/flox}$) and further are transgenic for the Cre-recombinase under the control of the endogenous and interferon-inducible Mx1 promoter will be used to test the efficacy of the telomerase gene therapy to treat Dyskeratosis congenital (DKC). To exclusively study the effects of TRF1 ablation in the hematopoietic compartment bone marrow will be transplanted from these mice into irradiated wild-type mice as described previously (Beier et al., 2012). One month after transplantation the mice will be injected via their tail vein with $4 \times 10^{12}$ AAV9 genomes carrying the mTERT cDNA under the control of the potent cytomegalovirus promoter (for virus production, see below 3.3). By analogy, empty AAV9 lacking the telomerase gene will be injected into a control group. Furthermore, to follow the viral tropism and transgene expression over time, a separate group of animals will be injected with AAV9-eGFP. One week after the virus infection TRF1 deletion in the bone marrow will be induced by long-term polyinosinic-polycytidylic acid (pI:pC) treatment with intraperitoneal injections every third day. pI:pC acts as immunostimulant and activates Cre expression which in turn leads to TRF1 deletion in approximately 50% of hematopoietic cells (upon each injection) with the above mentioned consequences (see 2). In contrast to pI:pC treatment, animal groups previously infected with AAV9-mTERT and AAV9-empty will not undergo pI:pC treatment to serve as additional control cohorts.

With this experimental design the dramatic telomere shortening, owed to compensatory proliferation in the remaining hematopoietic cells which have not lost TRF1, by ectopic expression of telomerase, will be reduced. The strongest measure to assess the effectiveness of the gene therapy is an extended life span by virtue of delayed or prevented bone marrow failure (end point of experiment=death of animals) Furthermore, successful telomerase treatment should show improvements with regards to overall fitness of the animals, i.e. no skin abnormalities and no anaemic pallor. The latter goes hand in hand with higher blood counts (leukocytes, lymphocytes, thrombocytes), which will be determined from peripheral blood samples. The efficacy of telomerase expression on the molecular level will include telomere length measurements. To so Q-FISH analysis from bone marrow tissue sections and high throughput Q-FISH analysis from peripheral blood samples will be performed. For the second, blood will be taken every three to four weeks throughout the course of the experiment. In this way not only absolute telomere length, but also the rate of telomere shortening over time can be determined. Moreover, attenuated or abolished replicative senescence and exhaustion of stem and progenitor cells in the hematopoietic compartment will be monitored by assessment of common senescent markers such as beta-galactosidase activity and p21 protein levels. These markers as well as γH2AX and phospho-CHK1, molecular markers for replicative stress, can then be correlated with telomere length and survival of the animals.

Example 2

Production of Viruses

AAV based viral vectors for transduction will be generated by triple transfection of HEK293T cells as described in (Matsushita et al., 1998). Briefly, to 80% confluence grown cells are co-transfected with plasmids (1) carrying the expression cassette flanked by the AAV9 viral ITRs, (2) a helper plasmid carrying the AAV rep2 and cap9 genes, and (3) a plasmid carrying the adenovirus helper functions. The expression cassettes harbour murine TERT under the control of CMV promoter plus 3'-UTR (AAV9-mTERT), CMV promoter (AAV9-empty) alone and eGFP under the control of CMV promoter and SV40 polyA signal (AAV9-eGFP). Vectors are purified following an optimised method based on two consecutive cesium chloride gradients (Ayuso et al., 2010). Titres of viral genomes particles are determined by quantitative real time PCR. Viruses can be stably kept at −80° C. until infection of animals

Example 3

Telomere Analysis

Telomere Q-FISH Analysis on Paraffin Sections

Q-FISH determination on paraffin-embedded tissue sections mice are hybridized with a PNA-telomeric probe, and fluorescence intensity of telomeres are determined as described (Gonzalez-Suarez, Samper et al. 2001). Quantitative image analysis is performed using the Definiens Developer Cell software (version XD 1.2; Definiens AG). For statistical analysis a two-tailed Student t test is used to assess significance (GraphPad Prism software).

Quantitative Real-Time RT-PCR

Total RNA from tissues is extracted with Trizol (Life Technologies). RNA samples are DNase I treated and are used as template for a reverse transcription reaction using random primers and Superscript Reverse Transcriptase (Life Technologies), according to the manufacturer's guidelines. Quantitative real-time PCR is performed using an AB I PRISM 7700 (Applied Biosystems), using DNA Master SYBR Green I mix (Applied Biosystems).

The primers:

```
Actin-For:
                                       (SEQ ID NO: 7)
GGCACCACACCTTCTACAATG;

Actin-Rev:
                                       (SEQ ID NO: 8)
GTGGTGGTGAAGCTGTAG;

TERT-For:
                                       (SEQ ID NO: 9)
GGATTGCCACTGGCTCCG;

TERT-Rev:
                                       (SEQ ID NO: 10)
TGCCTGACCTCCTCTTGTGAC.

p16-For:
                                       (SEQ ID NO: 11)
CGTACCCCGATTCAGGTGAT
```

```
-continued
p16-Rev:
                                       (SEQ ID NO: 12)
TTGAGCAGAAGAGCTGCTACGT Axin2-For:
                                       (SEQ ID NO: 13)
GGCAAAGTGGAGAGGATCGAC Axin2-Rev:
                                       (SEQ ID NO: 14)
TCGTGGCTGTTGCGTAGG Cyclin D1-For:
                                       (SEQ ID NO: 15)
TGCGCCCTCCGTATCTTAC Cyclin D1-Rev:
                                       (SEQ ID NO: 16)
ATCTTAGAGGCCACGAACATGC CD44-For:
                                       (SEQ ID NO: 17)
CAGCCTACTGGAGATCAGGATGA CD44-Rev:
                                       (SEQ ID NO: 18)
GGAGTCCTTGGATGAGTCTCGA KIf4-For:
                                       (SEQ ID NO: 19)
GCGAACTCACACAGGCGAGAAACC KIf4-Rev:
                                       (SEQ ID NO: 20)
TCGCTTCCTCTTCCTCCGACACA Tieg1-For:
                                       (SEQ ID NO: 21)
CCCATTGCCCCTGCTCCTG Tieg1-Rev:
                                       (SEQ ID NO: 22)
TGTGTCCGCCGGTGTCTGG
```

Statistical analyses (Student's t-test) is performed on the Ct values as described before (Munoz, Blanco et al. 2005).

Example 4

Telomerase Gene Therapy in Aplastic Anemia

Mice and Animal Procedures

Mice were of pure C57/BL6 background and were produced and housed at the specific pathogen-free (SPF) animal house of the CNIO in Madrid, Spain. Trf1$^{lox/lox}$ Mx1-Cre and Trf1$^{lox/lox}$ Mx1-wt mice were generated previously described (Martinez et al., 2009) ENREF 20. For bone marrow transplantation 10 weeks old Trf1$^{lox/lox}$ Mx1-Cre mice were used as bone marrow donors for transplantation into 8 weeks old lethally (12Gy) irradiated wild-type mice as previously described (Beier et al., 2012, Samper et al., 2002). A total of 2 million cells were transplanted via tail vein injection at a donor:recipient ratio of 1:8 and mice were left for a latency period of 30 days to allow bone marrow reconstitution. To induce Cre expression, mice were intraperitoneally injected with polyinosinic-polycytidylic acid (pI:pC; Sigma-Aldrich) (15 ug/g body weight) 3 times per week for a total duration of 5 weeks. Mice were left for an additional week before they were randomly assigned to two groups for the treatment with AAV9-Tert or AAV9-empty gene therapy vectors. Vectors were administered via tail vein injection at a concentration of 4×10E12 viral genomes per mouse.

Gene Therapy Vector Production

Viral vectors were generated as described previously (Matsushita et al., 1998) and purified described in (Ayuso et al., 2010). Briefly, vectors were produced through triple transfection of HEK293T. Cells were grown in roller bottles (Corning, N.Y., USA) in Dulbecco's Modified Eagle's Medium supplemented with FBS (10% v/v) to 80% confluence and then co-transfected with: plasmid-1 carrying the expression cassette for gene of interest flanked by the AAV2 viral ITRs; plasmid-2 carrying the AAV rep2 and cap9 genes; plasmid-3 carrying the adenovirus helper functions (plasmids were kindly provided by K. A. High, Children's Hospital of Philadelphia). Expression cassettes were under the control of the cytomegalovirus (CMV) promoter and contained a SV40 polyA signal for EGFP and the CMV promoter and the 3'UTR of the Tert gene as polyA signal for Tert. AAV9 particles were purified following an optimized method using two caesium chloride gradients, dialysed against PBS, filtered and stored at −80° C. until use (Ayuso et al., 2010). Viral genomes particles titres were determined by a standardized quantitative real time PCR method (Ayuso et al., 2014) and primers specific for the CMV sequence:

```
CMV-Forward:
                              (SEQ ID NO: 23)
5'-CAATTACGGGGTCATTAGTTCATAGC;

CMV-Reverse:
                              (SEQ ID NO: 24)
5'-ATACGTAGATGTACTGCCAAGTAGGA.
```

Histology

Bone marrow samples (sternum or tibia bone) were fixed in phosphate-buffered 4% formaldehyde and bones after decalcification paraffin embedded. 5 µm tissue sections were stained with Hematoxylin-Eosin for histological bone marrow assessment Immunohistochemistry was performed on deparaffinized tissues sections. After antigen retrieval samples were processed with the anti-EGFP antibodies (rabbit anti-EGFP, 1:200; Abcam, ab290). EGFP positive cells were counted in a semi automated way using ImageJ software.

FACS Sorting

For sorting of HSCs whole bone marrow cells were extracted from the long bones (femur & tibia) as previously described (Samper et al., 2002). Erythrocytes were lysed by incubating cells for 10 min in 10 ml erythrocyte lysis buffer (Roche), washed once with 10 ml PBS, and resuspended in FACS buffer (PBS, 2 mM EDTA, 0.3% BSA) containing Fc-block (1:400) at a concentration of 5-10×10^6 cell/100 µl. Cells were incubated for 10 min and washed once in FACS buffer. Cells were then resuspended in FACS buffer at 20-25×10^6 cell/ml and the antibody cocktail was added as follows: Anti-sca-1-PerCP-Cy5.5 (1:200), lin cocktail-eFluor450 (1:50) (all eBioscience), and anti-c-kit-APC-H7 (1:100) (BD Pharmingen). Cells were incubated for 30 min. After washing cells twice with PBS, 2 L of DAPI (200 g/mL) was added and cells were subsequently sorted in a FACS ARIA IIu (Becton Dickinson, San Jose, Calif.) into HSCs (lin negatice, sca1 and c-kit positive) and lineage positive (lin positive) fractions.

Colony Forming Assay

Short-term colony-forming assay (CFA) was performed by plating $1 \times 10^4$ and $2 \times 10^4$ freshly isolated mononucleated bone marrow cells (erythrocytes were lysed as described above) in 35-mm dishes (StemCell Technologies) containing Methocult (methylcellulose-based) media (StemCell Technologies) as described in the manufacturer's protocol. All experiments were performed in duplicates and the numbers of colonies formed were counted after 12 days incubation at 37° C.

Blood Counts

Peripheral blood was drawn from the facial vein (~50 µl) and collected into anti-coagulation tubes (EDTA). Blood counts were determined using an Abacus Junior Vet veterinary hematology analyzer.

Quantitative Real-Time PCR and Western Blots

Total RNA from whole bone marrow extracts or FACS sorted bone marrow cells was isolated using Qiagen's RNeasy mini kit according to the manufacturer protocol. The optional DNaseI digest was always performed. Quantitative real-time PCR was performed using an ABI PRISM 7700 or QuantStudio 6 Flex (both Applied Biosystems). Primers sequences for Tert and reference genes Act1 and TBP are as follows:

```
Tert-Forward
                              (SEQ ID NO: 9)
5'GGATTGCCACTGGCTCCG;

Tert-Reverse
                              (SEQ ID NO: 10)
5'TGCCTGACCTCCTCTTGTGA;

Actin-Forward
                              (SEQ ID NO: 7)
5'GGCACCACACCTTCTACAATG;

Actin-Reverse
                              (SEQ ID NO: 8)
5'GTGGTGGTGAAGCTGTAG;

TBP-Forward
                              (SEQ ID NO: 25)
5'CTTCCTGCCACAATGTCACAG;

TBP-Reverse
                              (SEQ ID NO: 26)
5'CCTTTCTCATGCTTGCTTCTCTG.
```

Q-FISH Telomere Analysis

Q-FISH analysis on bone marrow tissues sections was performed as described previously (Samper et al., 2000). Briefly, tissues sections were post fixed in 4% formaldehyde for 5 min, washed 3×5 min in PBS and incubated at 37° C. for 15 min in pepsin solution (0.1% Porcine Pepsin, Sigma; 0.01M HCl, Merck). Washes and fixation was repeated and slides dehydrated in a 70%-90%-100% ethanol series (5 min each). Slides were 10 min air-dried and 30 µl of telomere probe mix added to each slide (10 mM TrisCl pH 7, 25 mM MgCl2, 9 mM citric acid, 82 mM Na2HPO4, 70% deionized formamide (Sigma), 0.25% blocking reagent (Roche) and 0.5 mg/ml Telomeric PNA probe (Panagene)), a cover slip added and slides incubated for 3 min at 85° C., and 2 h at room temperature in a wet chamber in the dark. Slides were washed 2×15 min in 10 mM TrisCl pH 7, 0.1% BSA in 70% formamide under vigorous shaking, then 3×5 min in TBS 0.08% Tween20, and then incubated in a 40,6-diamidino-2-phenylindole (DAPI) bath (4 mg/ml 1 DAPI (Sigma) in PBS). Samples were mounted in Vectashield (Vector™). Confocal image were acquired as stacks every 0.5 µm for a total of 1.5 µm using a Leica SP5-MP confocal microscope and maximum projections were done with the LAS-AF software. Telomere signal intensity was quantified using Definiens software.

High throughput (HT)-Q-FISH on peripheral blood leukocytes was done as described (Canela et al., 2007a). Briefly, 120-150 µl of blood were extracted from the facial vein. Erythrocytes were lysed (Erythrocyte lysis buffer, Qiagen) and 30-90 k leukocytes were plated in duplicate into clear-bottom, black-walled 96-well plates pre-coated for 30 min with 0.001% poly-L-lysine. Plates were incubated at 37° C. for 2 h and fixed with methanol/acetic acid (3:1, v/v) 2×10 min and overnight at −20° C. Fixative was removed, plates dried for at least 1 h at 37° C. and samples were rehydrated in PBS. Plates were then subjected to a standard Q-FISH protocol (see above) using a telomere-specific PNA-CY3 probe; DAPI was used to stain nuclei. Sixty images per well were captured using the OPERA (Perkin Elmer) High-Content Screening system. TL values were analysed using individual telomere spots (>10,000 telomere spots per sample). The average fluorescence intensities of each sample were converted into kilobase using L5178-R and L5178-S cells as calibration standards, which have stable TLs of 79.7 and 10.2 kb, respectively. Samples were analyzed in duplicate.

AAV9-Tert Targets Bone Marrow and Hematopoietic Stem Cells

First, we set out to address the capability of AAV9 vectors to transduce the bone marrow upon intravenous injection by using both a AAV9-EGFP reporter virus, which allows determination of the location and percentage of AAV9-transduced cells, as well as by determining Tert mRNA expression in vivo in different bone marrow cell populations following AAV9-Tert treatment. To this end, we first injected wild-type mice with AAV9-EGFP particles at a concentration of 3.5E12 viral genomes per mouse through tail vein injections. Immunohistochemistry analysis of bone marrow section with specific anti-EGFP antibodies revealed 2% positive EGFP expressing cells in the middle bone sections and this was increased up to 10% in the regions adjacent to the joints, which were the ones showing the highest AAV9-transduction. We then injected wild-type mice with the same amount of AAV9-Tert particles and determined Tert mRNA expression by RT-PCR in whole bone marrow isolates at two weeks and 8 months after virus injection. As soon as two weeks post-treatment with the AAV9 vectors, we found increased Tert mRNA expression in the AAV9-Tert treated mice compared to those treated with the AAV9 empty vector and this difference was maintained still 8 months after initial treatment. We then studied Tert mRNA expression specifically in the blood-forming cells of the bone marrow. To this end, we performed FACS sorting of c-kit and Sca-1 positive HSCs cells and lin-positive lineage committed cells. We found a significant increase in both HSCs (10 fold) and lineage committed bone marrow cells (3.5 fold) in Tert mRNA in AAV9-Tert treated mice compared to mice treated with the empty vector, demonstrating that bone marrow cells including HSCs cells are targeted by Tert gene therapy. Given that we achieved increased Tert expression in HSCs, we next addressed whether this affected their stem cell potential. To this end, we performed a colony forming cell assay (MethoCult) Interestingly, we observed significantly increased number of colonies in the AAV9-Tert mice compared to the empty vector controls.

In summary these data suggest that AAV9 administered at a high dose can target hematopoietic cells and that these enhances the proliferation capacity of those cells.

AAV9-Tert Treatment in a Mouse Model of Aplastic Anemia Resecues Survival

We next tested whether treatment with AAV9-Tert is effective in increasing survival upon induction of lethal aplastic anemia owing to critically short telomeres (Beier et al., 2012). In particular, we used a conditional Trf1 mouse model recently developed by us in which we lethally irradiate wild-type mice and transplant them with bone marrow isolated from Trf1$^{lox/lox}$ Mx1-Cre mice to exclusively study the effects on bone marrow. Trf1 deletion can be induced by administration of pI:pC and subsequent expression of the Cre recombinase (Beier et al., 2012). Cells depleted for Trf1 die and are rapidly removed from the bone marrow, while cells that remain with intact Trf1 undergo compensatory rounds of cell division which leads to rapid telomere shortening, follow by replicative senescence and finally results in bone marrow failure. In the specific experimental settings here we induced Trf1 deletion by injecting mice 3 times per week with pI:pC for a total period of 5 weeks, at which point these mice start showing signs of aplastic anemia (Beier et al., 2012). One week after we stopped the induction of Trf1 deletion, mice were subjected to gene therapy treatment with AAV9-Tert or AAV9-empty control vectors. We monitored the survival of these mice for 100 days following the treatment with the AAV9 vectors. Strikingly, AAV9-Tert treatment drastically improved survival (87%) compared with mice treated with the empty vector (55%) (FIG. 1A). In particular, while only 4 mice injected with AAV9-Tert developed aplastic anemia during this time (13%), 16 mice of the control group (44%) died with clear signs of aplastic anemia (FIG. 1B,C). In agreement with the anemic appearance blood count analysis from these mice (blood drawn from AAV9-empty and AAV9-Tert upon sacrificing) showed a drastic drop in platelet count and haemoglobin level compared with mice without signs of aplastic anemia (FIG. 1D, E). Post mortem histopathologic analysis of bone marrow sections from mice that died during the first 100 days further confirmed the aplastic anemia phenotype. In particular, mice presented with severe bone marrow hypo- and aplasia in 2 or all 3 blood lineages. While the diagnosis at the point of death in both groups was marrow bone failure and aplasia the phenotype appeared milder in the AAV9-Tert group compared with the AAV9-empty group as seen by higher bone marrow cellularity.

Our results suggest that AAV9-Tert gene therapy significantly reduces aplastic anemia mortality by preventing the loss of blood forming hematopoietic cells.

Figure 2:
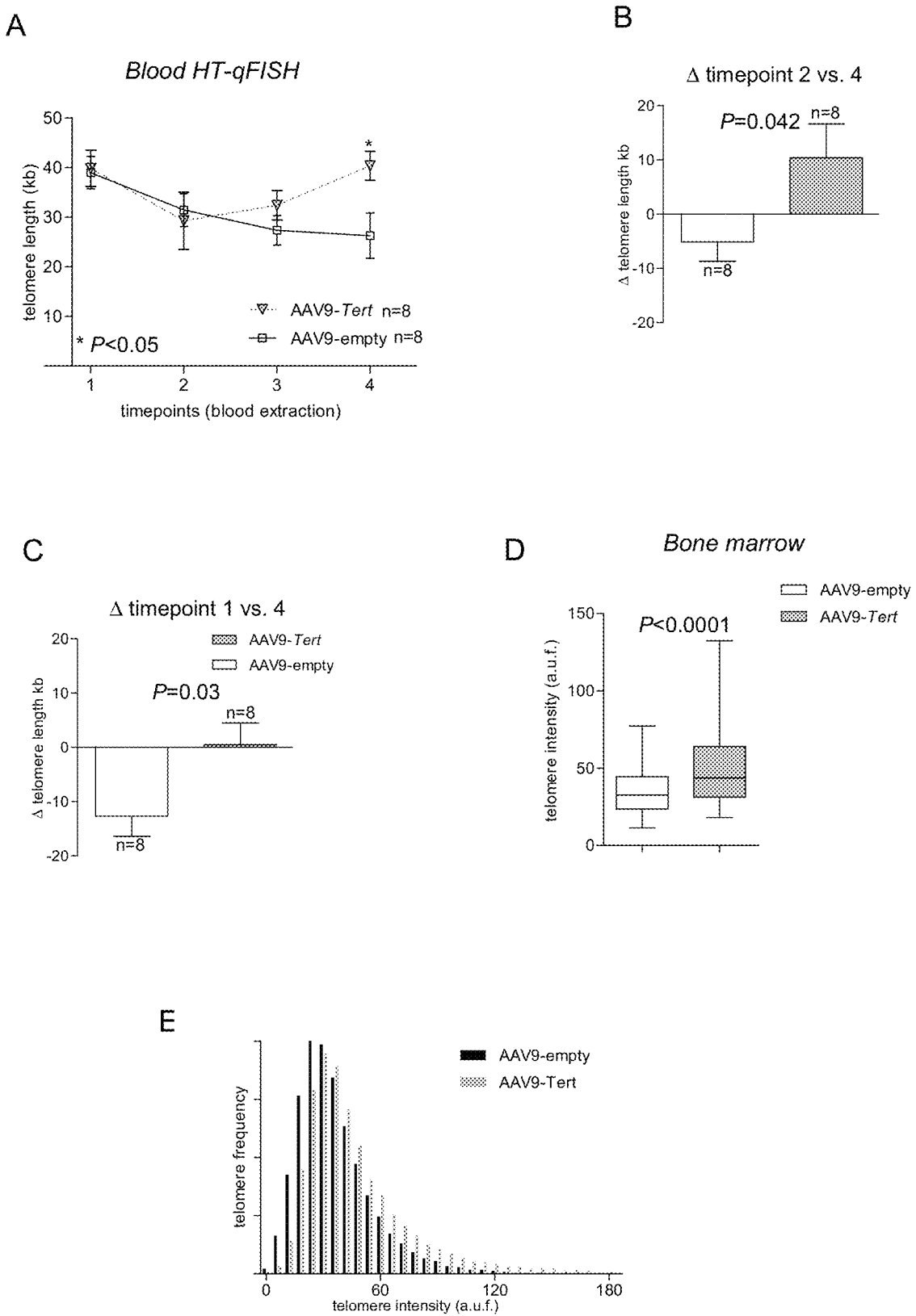
FIG. 2: AAV9-Tert effects on telomere length in peripheral blood (A-C) and bone marrow (D-E)

Telomerase Treatment Leads to Telomere Elongation in Peripheral Blood and Bone Marrow Because the aplastic anemia phenotype in our mouse model is caused by the loss of telomeres, we next compared telomere length in mice treated with telomerase to mice receiving the control vector. First we used HT-Q-FISH technology (Canela et al., 2007b) to follow telomere length in peripheral blood monocytes in a longitudinal manner. To do so, we extracted blood at 4 different time points; after bone marrow engraftment (1), after pI:pC treatment (2), 2 months after AAV9 injection (3) and 4 months after AAV9 injection (4). As expected we found that telomere length between time point 1 and 2 in both groups drops by approximately 10 kb which is owed to the pI:pC treatment. While telomere length in the AAV9-empty group between time point 2 and 4 continuous to slightly shorten, AAV9-Tert treatment led to a net increase in average telomere of 10 kb (FIG. 2A,B). Throughout the course of this experiment AAV9-empty treated mice showed an average telomere length loss of 12 kb, whereas in AAV9-Tert treated mice telomeres were re-elongated to similar levels as before the pI:pC treatment (FIG. 2C). Next we performed Q-FISH analysis on bone marrow cross-sections. In agreement with longer telomere length in peripheral blood we found that AAV9-Tert treated mice had significantly longer telomeres compared with empty vector treated mice (FIG. 2D, E).

REFERENCES

Armanios, M. (2012). An emerging role for the conserved telomere component 1 (CTC1) in human genetic disease. Pediatr Blood Cancer 59, 209-210.

Armanios, M., and Blackburn, E. H. (2012). The telomere syndromes. Nature reviews. Genetics 13, 693-704.

Ayuso, E., Mingozzi, F., Montane, J., Leon, X., Anguela, X. M., Haurigot, V., Edmonson, S. A., Africa, L., Zhou, S., High, K. A., et al. (2010). High AAV vector purity results in serotype- and tissue-independent enhancement of transduction efficiency. Gene therapy 17, 503-510.

Beier, F., Foronda, M., Martinez, P., and Blasco, M. A. (2012). Conditional TRF1 knockout in the hematopoietic compartment leads to bone marrow failure and recapitulates clinical features of Dyskeratosis congenita. Blood.

Bernardes de Jesus, B., Vera, E., Schneeberger, K., Tejera, A. M., Ayuso, E., Bosch, F., and Blasco, M. A. (2012). Telomerase gene therapy in adult and old mice delays aging and increases longevity without increasing cancer. EMBO molecular medicine 4, 691-704.

Bernardes de Jesus de Jesus, B. and Blasco, M. A, (2013). Telomerase at the intersection of cancer and aging. Trends Genet. 29, 513-520.

Blasco, M. A. (2007). Telomere length, stem cells and aging. Nature chemical biology 3, 640-649.

Blasco, M. A., Lee, H. W., Hande, M. P., Samper, E., Lansdorp, P. M., DePinho, R. A., and Greider, C. W. (1997). Telomere shortening and tumor formation by mouse cells lacking telomerase RNA. Cell 91, 25-34.

Buning, H., Perabo, L., Coutelle, O., Quadt-Humme, S., and Hallek, M. (2008). Recent developments in adeno-associated virus vector technology. The journal of gene medicine 10, 717-733.

Calado, R. T., Yewdell, W. T., Wilkerson, K. L., Regal, J. A., Kajigaya, S., Stratakis, C. A., and Young, N. S. (2009). Sex hormones, acting on the TERT gene, increase telomerase activity in human primary hematopoietic cells. Blood 114, 2236-2243.

Callen, E., Samper, E., Ramirez, M. J., Creus, A., Marcos, R., Ortega, J. J., Olive, T., Badell, I., Blasco, M. A., and Surralles, J. (2002). Breaks at telomeres and TRF2-independent end fusions in Fanconi anemia. Hum Mol Genet 11, 439-444.

Carroll, K. A., and Ly, H. (2009). Telomere dysfunction in human diseases: the long and short of it! International journal of clinical and experimental pathology 2, 528-543.

Dokal, I. (2011). Dyskeratosis congenita. Hematology/the Education Program of the American Society of Hematology. American Society of Hematology. Education Program 2011, 480-486.

Dokal, I., and Vulliamy, T. (2010). Inherited bone marrow failure syndromes. Haematologica 95, 1236-1240.

Duque, S., Joussemet, B., Riviere, C., Marais, T., Dubreil, L., Douar, A. M., Fyfe, J., Moullier, P., Colle, M. A., and Barkats, M. (2009). Intravenous administration of self-complementary AAV9 enables transgene delivery to adult motor neurons. Molecular therapy: the journal of the American Society of Gene Therapy 17, 1187-1196.

Foust, K. D., Nurre, E., Montgomery, C. L., Hernandez, A., Chan, C. M., and Kaspar, B. K. (2009). Intravascular AAV9 preferentially targets neonatal neurons and adult astrocytes. Nat Biotechnol 27, 59-65.

Gadalla, S. M., Cawthon, R., Giri, N., Alter, B. P., and Savage, S. A. (2010). Telomere length in blood, buccal cells, and fibroblasts from patients with inherited bone marrow failure syndromes. Aging (Albany N.Y.) 2, 867-874.

Gao, G. P., Alvira, M. R., Wang, L., Calcedo, R., Johnston, J., and Wilson, J. M. (2002). Novel adeno-associated viruses from rhesus monkeys as vectors for human gene therapy. Proc Natl Acad Sci USA 99, 11854-11859.

Gonzalez-Suarez, E., Samper, E., Ramirez, A., Flores, J. M., Martin-Caballero, J., Jorcano, J. L., and Blasco, M. A. (2001). Increased epidermal tumors and increased skin wound healing in transgenic mice overexpressing the catalytic subunit of telomerase, mTERT, in basal keratinocytes. EMBO J 20, 2619-2630.

Herrera, E., Samper, E., Martin-Caballero, J., Flores, J. M., Lee, H. W., and Blasco, M. A. (1999). Disease states associated with telomerase deficiency appear earlier in mice with short telomeres. EMBO J 18, 2950-2960.

Holme, H., Hossain, U., Kirwan, M., Walne, A., Vulliamy, T., and Dokal, I. (2012). Marked genetic heterogeneity in familial myelodysplasia/acute myeloid leukaemia. British journal of haematology 158, 242-248.

Inagaki, K., Fuess, S., Storm, T. A., Gibson, G. A., McTiernan, C. F., Kay, M. A., and Nakai, H. (2006). Robust systemic transduction with AAV9 vectors in mice: efficient global cardiac gene transfer superior to that of AAV8. Molecular therapy: the journal of the American Society of Gene Therapy 14, 45-53.

Jaime-Perez, J. C., Colunga-Pedraza, P. R., Gomez-Ramirez, C. D., Gutierrez-Aguirre, C. H., Cantu-Rodriguez, O. G., Tarin-Arzaga, L. C., and Gomez-Almaguer, D. (2011). Danazol as first-line therapy for aplastic anemia. Annals of hematology 90, 523-527.

Jaskelioff, M., Muller, F. L., Paik, J. H., Thomas, E., Jiang, S., Adams, A. C., Sahin, E., Kost-Alimova, M., Protopopov, A., Cadinanos, J., et al. (2011). Telomerase reactivation reverses tissue degeneration in aged telomerase-deficient mice. Nature 469, 102-106.

Jiang, H., Lillicrap, D., Patarroyo-White, S., Liu, T., Qian, X., Scallan, C. D., Powell, S., Keller, T., McMurray, M., Labelle, A., et al. (2006). Multiyear therapeutic benefit of AAV serotypes 2, 6, and 8 delivering factor VIII to hemophilia A mice and dogs. Blood 108, 107-115.

Kaplitt, M. G. (2009). Gene therapy clinical trials in the human brain. Protocol development and review of current applications. Frontiers of neurology and neuroscience 25, 180-188.

Kee, Y., and D'Andrea, A. D. (2012). Molecular pathogenesis and clinical management of Fanconi anemia. J Clin Invest 122, 3799-3806.

Lee, H. W., Blasco, M. A., Gottlieb, G. J., Homer, J. W., 2nd, Greider, C. W., and DePinho, R. A. (1998). Essential role of mouse telomerase in highly proliferative organs. Nature 392, 569-574.

Maguire, A. M., Simonelli, F., Pierce, E. A., Pugh, E. N., Jr., Mingozzi, F., Bennicelli, J., Banfi, S., Marshall, K. A., Testa, F., Surace, E. M., et al. (2008). Safety and efficacy of gene transfer for Leber's congenital amaurosis. The New England journal of medicine 358, 2240-2248.

Manno, C. S., Pierce, G. F., Arruda, V. R., Glader, B., Ragni, M., Rasko, J. J., Ozelo, M. C., Hoots, K., Blatt, P., Konkle, B., et al. (2006). Successful transduction of liver in hemophilia by AAV-Factor IX and limitations imposed by the host immune response. Nature medicine 12, 342-347.

Martinez, P., and Blasco, M. A. (2011). Telomeric and extra-telomeric roles for telomerase and the telomere-binding proteins. Nature reviews. Cancer 11, 161-176.

Mas, A., Montane, J., Anguela, X. M., Munoz, S., Douar, A. M., Riu, E., Otaegui, P., and Bosch, F. (2006). Reversal of type 1 diabetes by engineering a glucose sensor in skeletal muscle. Diabetes 55, 1546-1553.

Mason, P. J., and Bessler, M. (2011). The genetics of dyskeratosis congenita. Cancer genetics 204, 635-645.

Matsushita, T., Elliger, S., Elliger, C., Podsakoff, G., Villarreal, L., Kurtzman, G. J., Iwaki, Y., and Colosi, P. (1998). Adeno-associated virus vectors can be efficiently produced without helper virus. Gene therapy 5, 938-945.

Mavilio, F. (2012). Gene therapies need new development models. Nature 490,7.

Niemeyer, G. P., Herzog, R. W., Mount, J., Arruda, V. R., Tillson, D. M., Hathcock, J., van Ginkel, F. W., High, K. A., and Lothrop, C. D., Jr. (2009). Long-term correction of inhibitor-prone hemophilia B dogs treated with liver-directed AAV2-mediated factor IX gene therapy. Blood 113, 797-806.

O'Reilly, M., Shipp, A., Rosenthal, E., Jambou, R., Shih, T., Montgomery, M., Gargiulo, L., Patterson, A., and Corrigan-Curay, J. (2012). NIH oversight of human gene transfer research involving retroviral, lentiviral, and adeno-associated virus vectors and the role of the NIH recombinant DNA advisory committee. Methods in enzymology 507, 313-335.

Samper, E., Flores, J. M., and Blasco, M. A. (2001). Restoration of telomerase activity rescues chromosomal instability and premature aging in Terc−/−mice with short telomeres. EMBO Rep 2, 800-807.

Savage, S. A., and Alter, B. P. (2008). The role of telomere biology in bone marrow failure and other disorders. Mechanisms of ageing and development 129, 35-47.

Savage, S. A., Calado, R. T., Xin, Z. T., Ly, H., Young, N. S., and Chanock, S. J. (2006). Genetic variation in telomeric repeat binding factors 1 and 2 in aplastic anemia. Experimental hematology 34, 664-671.

Stroes, E. S., Nierman, M. C., Meulenberg, J. J., Franssen, R., Twisk, J., Henny, C. P., Maas, M. M., Zwinderman, A. H., Ross, C., Aronica, E., et al. (2008). Intramuscular administration of AAV1-lipoprotein lipase S447X lowers triglycerides in lipoprotein lipase-deficient patients. Arteriosclerosis, thrombosis, and vascular biology 28, 2303-2304.

Tafuro, S., Ayuso, E., Zacchigna, S., Zentilin, L., Moimas, S., Dore, F., and Giacca, M. (2009). Inducible adeno-associated virus vectors promote functional angiogenesis in adult organisms via regulated vascular endothelial growth factor expression. Cardiovascular research 83, 663-671.

Tomas-Loba, A., Flores, I., Fernandez-Marcos, P. J., Cayuela, M. L., Maraver, A., Tejera, A., Borras, C., Matheu, A., Klatt, P., Flores, J. M., et al. (2008). Telomerase reverse transcriptase delays aging in cancer-resistant mice. Cell 135, 609-622.

Walne, A. J., Vulliamy, T., Beswick, R., Kirwan, M., and Dokal, I. (2008). TINF2 mutations result in very short telomeres: analysis of a large cohort of patients with dyskeratosis congenita and related bone marrow failure syndromes. Blood 112, 3594-3600.

Yamaguchi, H., Baerlocher, G. M., Lansdorp, P. M., Chanock, S. J., Nunez, O., Sloand, E., and Young, N. S. (2003). Mutations of the human telomerase RNA gene (TERC) in aplastic anemia and myelodysplastic syndrome. Blood 102, 916-918.

Yamaguchi, H., Calado, R. T., Ly, H., Kajigaya, S., Baerlocher, G. M., Chanock, S. J., Lansdorp, P. M., and Young, N. S. (2005). Mutations in TERT, the gene for telomerase reverse transcriptase, in aplastic anemia. The New England journal of medicine 352, 1413-1424.

Ziegler, P., Schrezenmeier, H., Akkad, J., Brassat, U., Vankann, L, Panse, J., Wilop, S., Balabanov, S., Schwarz, K., Martens, U. M., and Brummendorf, T. H. (2012). Telomere elongation and clinical response to androgen treatment in a patient with aplastic anemia and a heterozygous hTERT gene mutation. Annals of hematology 91, 1115-1120.

Ayuso, E., V. Blouin, M. Lock, S. McGorray, X. Leon, M. R. Alvira, A. Auricchio, S. Bucher, A. Chtarto, K. R. Clark, C. Darmon, M. Doria, W. Fountain, G. Gao, K. Gao, M. Giacca, J. Kleinschmidt, B. Leuchs, C. Melas, H. Mizukami, M. Muller, Y. Noordman, O. Bockstael, K. Ozawa, C. Pythoud, M. Sumaroka, R. Surosky, L. Tenenbaum, I. Van der Linden, B. Weins, J. F. Wright, X. Zhang, L. Zentilin, F. Bosch, R. O. Snyder & P. Moullier, (2014) Manufacturing and Characterization of a Recombinant Adeno-Associated Virus Type 8 Reference Standard Material. Hum Gene Ther.

Ayuso, E., F. Mingozzi, J. Montane, X. Leon, X. M. Anguela, V. Haurigot, S. A. Edmonson, L. Africa, S. Zhou, K. A. High, F. Bosch & J. F. Wright, (2010) High AAV vector purity results in serotype- and tissue-independent enhancement of transduction efficiency. Gene Ther 17: 503-510.

Ball, S. E., F. M. Gibson, S. Rizzo, J. A. Tooze, J. C. Marsh & E. C. Gordon-Smith, (1998) Progressive telomere shortening in aplastic anemia. Blood 91: 3582-3592.

Beier, F., M. Foronda, P. Martinez & M. A. Blasco, (2012) Conditional TRF1 knockout in the hematopoietic compartment leads to bone marrow failure and recapitulates clinical features of Dyskeratosis congenita. Blood.

Bernardes de Jesus, B., E. Vera, K. Schneeberger, A. M. Tejera, E. Ayuso, F. Bosch & M. A. Blasco, (2012) Telomerase gene therapy in adult and old mice delays aging and increases longevity without increasing cancer. EMBO Mol Med 4: 1-14.

Blackburn, E. H., (2001) Switching and signaling at the telomere. Cell 106: 661-673.

Canela, A., P. Klatt & M. A. Blasco, (2007a) Telomere length analysis. Methods Mol Biol 371: 45-72.

Canela, A., E. Vera, P. Klatt & M. A. Blasco, (2007b) High-throughput telomere length quantification by FISH and its application to human population studies. Proc Natl Acad Sci USA 104: 5300-5305.

de Lange, T., (2005) Shelterin: the protein complex that shapes and safeguards human telomeres. Genes Dev 19: 2100-2110.

Dokal, I., (2011) Dyskeratosis congenita. Hematology Am Soc Hematol Educ Program 2011: 480-486.

Dokal, I. & T. Vulliamy, (2010) Inherited bone marrow failure syndromes. Haematologica 95: 1236-1240.

Flores, I., A. Canela, E. Vera, A. Tejera, G. Cotsarelis & M. A. Blasco, (2008) The longest telomeres: a general signature of adult stem cell compartments. Genes Dev 22: 654-667.

Flores, I., M. L. Cayuela & M. A. Blasco, (2005) Effects of telomerase and telomere length on epidermal stem cell behavior. Science 309: 1253-1256.

Harley, C. B., A. B. Futcher & C. W. Greider, (1990) Telomeres shorten during ageing of human fibroblasts. Nature 345: 458-460.

Hiyama, E. & K. Hiyama, (2007) Telomere and telomerase in stem cells. Br J Cancer 96: 1020-1024.

Maciejewski, J. P., S. Anderson, P. Katevas & N. S. Young, (1994) Phenotypic and functional analysis of bone marrow progenitor cell compartment in bone marrow failure. Br J Haematol 87: 227-234.

Marsh, J. C., S. E. Ball, J. Cavenagh, P. Darbyshire, I. Dokal, E. C. Gordon-Smith, J. Keidan, A. Laurie, A. Martin, J. Mercieca, S. B. Killick, R. Stewart & J. A. Yin, (2009) Guidelines for the diagnosis and management of aplastic anaemia. Br J Haematol 147: 43-70.

Martinez, P., M. Thanasoula, P. Munoz, C. Liao, A. Tejera, C. McNees, J. M. Flores, O. Fernandez-Capetillo, M. Tarsounas & M. A. Blasco, (2009) Increased telomere fragility and fusions resulting from TRF1 deficiency lead to degenerative pathologies and increased cancer in mice. Genes Dev 23: 2060-2075.

Matsushita, T., S. Elliger, C. Elliger, G. Podsakoff, L. Villarreal, G. J. Kurtzman, Y. Iwaki & P. Colosi, (1998) Adeno-associated virus vectors can be efficiently produced without helper virus. Gene Ther 5: 938-945.

Nakao, S., (1997) Immune mechanism of aplastic anemia. Int J Hematol 66: 127-134.

Samper, E., P. Fernandez, R. Eguia, L. Martin-Rivera, A. Bernad, M. A. Blasco & M. Aracil, (2002) Long-term repopulating ability of telomerase-deficient murine hematopoietic stem cells. Blood 99: 2767-2775.

Samper, E., F. A. Goytisolo, P. Slijepcevic, P. P. van Buul & M. A. Blasco, (2000) Mammalian Ku86 protein prevents telomeric fusions independently of the length of TTAGGG repeats and the G-strand overhang. EMBO Rep 1: 244-252.

Scopes, J., M. Bagnara, E. C. Gordon-Smith, S. E. Ball & F. M. Gibson, (1994) Haemopoietic progenitor cells are reduced in aplastic anaemia. Br J Haematol 86: 427-430.

Vulliamy, T., A. Marrone, I. Dokal & P. J. Mason, (2002) Association between aplastic anaemia and mutations in telomerase RNA. Lancet 359: 2168-2170.

Wynn, R. F., M. A. Cross, C. Hatton, A. M. Will, L. S. Lashford, T. M. Dexter & N. G. Testa, (1998) Accelerated telomere shortening in young recipients of allogeneic bone-marrow transplants. Lancet 351: 178-181.

We claim:

1. A method of treating a condition associated with aplastic anemia, the method comprising:
administering to a subject in need thereof an adeno-associated virus-based vector comprising at least a capsid and a nucleic acid encoding telomerase reverse transcriptase (TERT) operably linked to a regulatory sequence that drives the expression of the encoded TERT, wherein the method results in transduction of hematopoietic stem cells.

2. The method of claim 1, wherein TERT is encoded by a nucleic acid sequence comprising the sequence of SEQ ID NO: 1 or SEQ ID NO: 3.

3. The method of claim 1, wherein TERT comprises the amino acid sequence of SEQ ID NO:2 or SEQ ID NO: 4.

4. The method of claim 1, wherein the capsid is derived from serotype 9 adeno-associated virus (AAV9).

5. The method of claim 4, wherein nucleic acid is packaged in the AAV9 capsid and is flanked at both ends by the internal terminal repeats of the serotype 2 adeno-associated virus.

6. The method of claim 1, wherein the regulatory sequence is a constitutive promoter.

7. The method of claim 6, wherein the constitutive promoter is the cytomegalovirus (CMV) promoter.

* * * * *